(12) United States Patent
     Adler

(10) Patent No.: US 9,417,052 B2
(45) Date of Patent: Aug. 16, 2016

(54) OPTICAL COHERENCE TOMOGRAPHY CONTROL SYSTEMS AND METHODS

(71) Applicant: Desmond Adler, Concord, MA (US)

(72) Inventor: Desmond Adler, Concord, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 199 days.

(21) Appl. No.: 14/160,939

(22) Filed: Jan. 22, 2014

(65) Prior Publication Data

US 2014/0218742 A1    Aug. 7, 2014

Related U.S. Application Data

(63) Continuation of application No. 13/789,839, filed on Mar. 8, 2013, now Pat. No. 8,687,201.

(60) Provisional application No. 61/695,399, filed on Aug. 31, 2012.

(51) Int. Cl.
    *G01B 11/02* (2006.01)
    *G01B 9/02* (2006.01)
    (Continued)

(52) U.S. Cl.
    CPC .......... *G01B 9/02091* (2013.01); *A61B 5/0066* (2013.01); *G01B 9/02004* (2013.01);
    (Continued)

(58) Field of Classification Search
    CPC ............. G01B 9/02091; G01B 9/0209; G01B 9/02004; G01B 9/02067; A61B 5/0066; A61B 5/0084; H01S 3/0092; H01S 3/1062; H01S 3/1396
    USPC ........................................................ 356/497
    See application file for complete search history.

(56) References Cited

U.S. PATENT DOCUMENTS

| 3,431,514 A | 3/1969 | Harris et al. |
| 4,721,385 A | 1/1988 | Jelalian et al. |

(Continued)

FOREIGN PATENT DOCUMENTS

| EP | 2662683 | 11/2013 |
| WO | 2005047813 | 5/2005 |

(Continued)

OTHER PUBLICATIONS

Chinn et al., "Optical coherence tomography using a frequency-tunable optical source," Optics Letters 22:5, 340-342 (1997).

(Continued)

*Primary Examiner* — Tarifur Chowdhury
*Assistant Examiner* — Jonathon Cook
(74) *Attorney, Agent, or Firm* — K&L Gates LLP

(57) ABSTRACT

In part, the invention relates to methods, devices, and systems suitable for controlling a light source. The light source is configured for use in a data collection system such as an optical coherence tomography system. The light source can be controlled with a drive waveform. Linearizing and symmetrizing parameters of the light source such as forward and backward scan durations is achieved using a suitable drive waveform. Phase, amplitude, and other parameters for different harmonics of a fundamental wave can be identified that improve operating parameters such as the duty cycle and peak frequency matching between scans. The fundamental wave and one or more of such harmonics can be combined to generate the suitable drive wave form. The light source can include a tunable light source that includes or is in optical communication with a tunable filter.

23 Claims, 14 Drawing Sheets

(51) Int. Cl.
*A61B 5/00* (2006.01)
*H01S 3/106* (2006.01)
*H01S 3/139* (2006.01)
*H01S 5/183* (2006.01)
*H01S 3/00* (2006.01)

(52) U.S. Cl.
CPC ........... *G01B9/02067* (2013.01); *A61B 5/0084* (2013.01); *H01S 3/0092* (2013.01); *H01S 3/1062* (2013.01); *H01S 3/1396* (2013.01); *H01S 5/183* (2013.01)

(56) References Cited

U.S. PATENT DOCUMENTS

| | | | |
|---|---|---|---|
| 5,321,501 A | 6/1994 | Swanson et al. | |
| 5,459,570 A | 10/1995 | Swanson | |
| 5,465,147 A | 11/1995 | Swanson | |
| 5,509,093 A | 4/1996 | Miller et al. | |
| 5,513,204 A | 4/1996 | Jayaraman | |
| 5,748,598 A | 5/1998 | Swanson et al. | |
| 5,754,578 A | 5/1998 | Jayaraman | |
| 5,784,352 A | 7/1998 | Swanson et al. | |
| 5,835,517 A | 11/1998 | Jayaraman et al. | |
| 5,914,976 A | 6/1999 | Jayaraman et al. | |
| 5,956,355 A | 9/1999 | Swanson et al. | |
| 5,985,686 A | 11/1999 | Jayaraman | |
| 6,111,645 A | 8/2000 | Tearney et al. | |
| 6,122,417 A | 9/2000 | Jayaraman et al. | |
| 6,134,003 A | 10/2000 | Tearney et al. | |
| 6,160,826 A | 12/2000 | Swanson et al. | |
| 6,191,862 B1 | 2/2001 | Swanson et al. | |
| 6,282,011 B1 | 8/2001 | Tearney et al. | |
| 6,314,118 B1 | 11/2001 | Jayaraman et al. | |
| 6,341,137 B1 | 1/2002 | Jayaraman et al. | |
| 6,372,533 B2 | 4/2002 | Jayaraman et al. | |
| 6,421,164 B2 | 7/2002 | Tearney et al. | |
| 6,445,939 B1 | 9/2002 | Swanson et al. | |
| 6,485,413 B1 | 11/2002 | Boppart | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,816,515 B1 | 11/2004 | Yun et al. | |
| 6,879,851 B2 | 4/2005 | McNamara et al. | |
| 6,891,984 B2 | 5/2005 | Petersen et al. | |
| 6,901,087 B1 | 5/2005 | Richardson et al. | |
| 6,974,966 B1 | 12/2005 | Jayaraman | |
| 7,208,333 B2 | 4/2007 | Flanders et al. | |
| 7,241,286 B2 | 7/2007 | Atlas | |
| 7,414,779 B2 | 8/2008 | Huber et al. | |
| 7,415,049 B2 | 8/2008 | Flanders et al. | |
| 7,468,997 B2 | 12/2008 | Jayaraman | |
| 7,625,366 B2 | 12/2009 | Atlas | |
| 7,671,997 B2 | 3/2010 | Jayaraman et al. | |
| 7,733,497 B2 | 6/2010 | Yun et al. | |
| 7,843,976 B2 | 11/2010 | Cable et al. | |
| 7,848,791 B2 | 12/2010 | Schmitt et al. | |
| 7,880,882 B2 | 2/2011 | Jayaraman et al. | |
| 7,916,387 B2 | 3/2011 | Schmitt | |
| 7,935,060 B2 | 5/2011 | Schmitt et al. | |
| 8,315,282 B2 | 11/2012 | Huber et al. | |
| 8,325,419 B2 | 12/2012 | Schmitt | |
| 2005/0201662 A1 | 9/2005 | Petersen et al. | |
| 2005/0238067 A1 | 10/2005 | Choi | |
| 2006/0095065 A1 | 5/2006 | Tanimura et al. | |
| 2008/0165366 A1* | 7/2008 | Schmitt | A61B 5/0066 356/519 |
| 2011/0051143 A1 | 3/2011 | Flanders et al. | |
| 2012/0106579 A1 | 5/2012 | Roos et al. | |

FOREIGN PATENT DOCUMENTS

| | | |
|---|---|---|
| WO | 2006079078 | 7/2006 |
| WO | 2006130802 | 12/2006 |
| WO | 2010047936 | 4/2010 |
| WO | 2012093654 | 7/2012 |

OTHER PUBLICATIONS

Choma et al., "Sensitivity advantage of swept source and Fourier domain optical coherence tomography," Optics Express 11:18, 2183-2189 (2003).

Choma et al., "Swept source optical coherence tomography using an all-fiber 1300-nm ring laser source," Journal of Biomedical Optics 10:4, 044009-1-044009-6 (2005).

Huang et al., "Optical Coherence Tomography," Science 254: 1178-1181 (1991).

Huber et al., "Amplified, frequency swept lasers for frequency domain reflectometry and OCT imaging: design and scaling principles," Opt. Express 13:9, 3513-3528 (2005).

Huber et al., "Fourier Domain Mode Locking (FDML): A new laser operating regime and applications for optical coherence tomography," Optics Express 14:8, 3225-3237 (2006).

Yun et al., "High-speed spectral-domain optical coherence tomography at 1.3 µm wavelength," Optics Express 11:26, pp. 3598-3604 (2003).

International Search Report and Written Opinion of the International Searching Authority for International Application No. PCT/US2008/000341, mailed Jun. 25, 2008 (12 pgs.).

Ho et al., "Spectrum of Externally Modulated Optical Signals," Journal of Lightwave Technology 22:2, pp. 658-663 (Feb. 2004).

Adler et al., "Phase-sensitive optical coherence tomography at up to 370,000 lines per second using buffered Fourier domain mode-locked lasers," Optics Letters 32:6, pp. 626-628 (Mar. 15, 2007).

Avanaki et al., "Algorithm for Excitation Optimization of Fabry-Perot Filters Used in Swept Sources" IEEE Photonics Technology Letters vol. 25, No. 5, pp. 472-475, Mar. 1, 2013.

International Search Report and Written Opinion for International Application No. PCT/US2013/056988 mailed from the International Searching Authority on Nov. 29, 2013 (15 pages).

Huber et al., "Fourier Domain Mode Locked Lasers for OCT imaging at up to 290 kHz sweep rates," SPIE-OSA 5861, pp. 1B-1-1B-6.

* cited by examiner

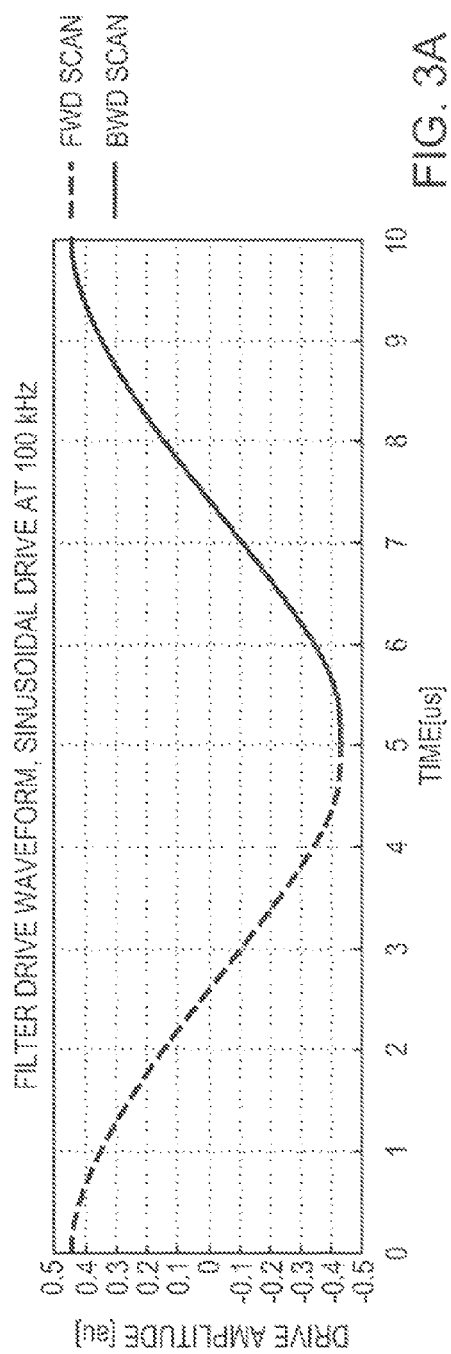
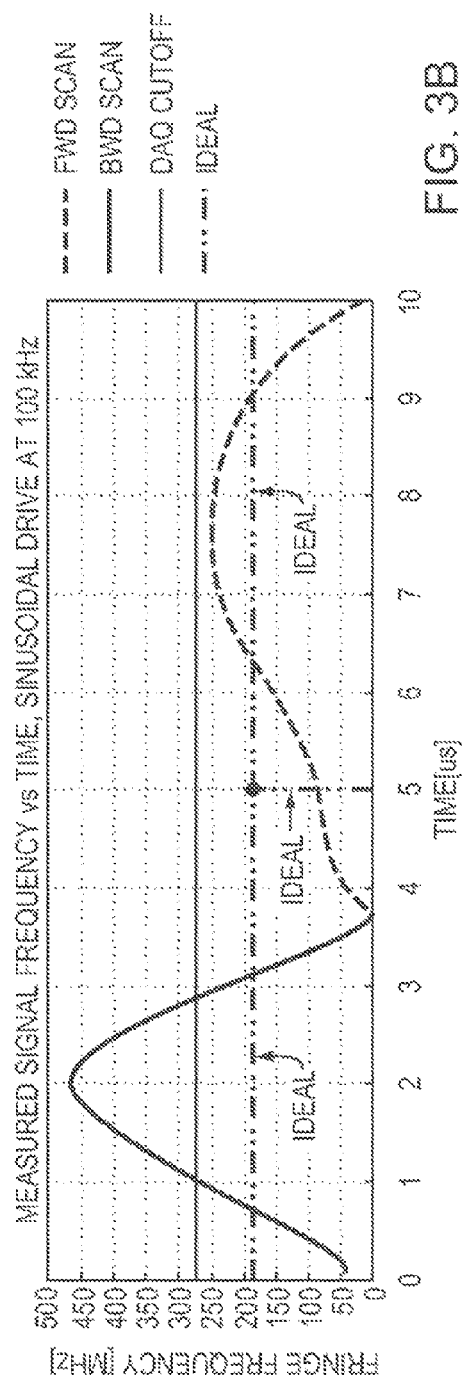
FIG. 3A
FIG. 3B

OPTICAL COHERENCE TOMOGRAPHY CONTROL SYSTEMS AND METHODS

RELATED APPLICATIONS

This application is a continuation of U.S. patent application Ser. No. 13/789,839 filed Mar. 8, 2013 which claims the benefit of priority under 35 U.S.C. 119(e) from U.S. Provisional Application No. 61/695,399 filed on Aug. 31, 2012 the disclosures of which are herein incorporated by reference in their entirety.

BACKGROUND

Optical coherence tomography (OCT) is an interferometric imaging technique with widespread applications in ophthalmology, cardiology, gastenterology and other fields of medicine. Huang D, Swanson E A, Lin C P, Schuman J S, Stinson W G, Chang W, Hee M R, Flotte T, Gregory K, Puliafito C A, and Fujimoto J G, "Optical coherence tomography," *Science*, Vol 254, 1178-1181 (1991). The ability to view subsurface structures with high resolution (2-15 µm) through small-diameter fiber-optic probes makes OCT especially useful for minimally invasive imaging of internal tissues and organs.

Time-domain OCT systems employ a broadband light source as an input to an interferometer with a mechanically actuated reference arm for path-length scanning. The interference signals generated by reflections from structures at different depths are measured point-by-point as the reference path length changes. In this measurement scheme, the maximum scanning speed is limited both by the dynamic mechanical constraints of the actuator and by the spectral power density of the light source. In such a system using a superluminescent light source that emits an output power of 25 mW over a spectral bandwidth of 40-60 nm, the maximum depth-scanning velocity that can be achieved while maintaining an adequate signal-to-noise ratio for tissue imaging (>90 dB) is approximately 25 m/s. Therefore, 512-line images of a 5 mm deep object can be acquired at a rate no greater than 10 per second.

Frequency-domain (also called Fourier-domain) (FD) OCT overcomes these speed constraints by taking advantage of optical frequency discrimination methods based on Fourier transformation, which eliminate the need for long-range mechanical actuators. Swanson E A and Chinn S R, "Method and Apparatus for Performing Optical Frequency Domain Reflectometry" U.S. Pat. No. 6,160,826 (issued Dec. 12, 2000), Choma M A, Sarunic M V, Yang C, and Izatt J, "Sensitivity advantage of swept source and Fourier domain optical coherence tomography," *Opt. Express*, Vol. 11, 2183-2189 (2003).

Instead of wasting available source power by interrogating the sample point-by-point, FD-OCT collects information from multiple depths simultaneously and discriminates reflections from different depths according to the optical frequencies of the signals they generate. FD-OCT systems based on swept-frequency light sources have attracted the most attention for medical applications that require subsurface imaging in highly scattering tissues.

The feasibility of swept-source OCT (SS-OCT) has been demonstrated in several academic research studies. Chinn S R, Swanson E A, and Fujimoto J G, "Optical coherence tomography using a frequency-tunable optical source," *Opt. Lett*. Vol. 22, 340-342 (1997); Yun S H, Tearney G J, Bouma B E, Park B H, de Boer J F, "High-speed spectral domain optical coherence tomography at 1.3 µm wavelength," *Optics Express*, Vol. 11, pp. 3598-3604 (2003); Choma M A, Hsu K, and Izatt J, "Swept source optical coherence tomography using an all-fiber 1300 nm ring laser source," *J. Biomed. Optics*, Vol. 10, p. 044009 (2005); Huber R. Wojtkowski, Taira K, Fujimoto J G, and Hsu K. "Amplified, frequency-swept lasers for frequency domain reflectometry and OCT imaging: design and scaling principles," *Opt. Express*, Vol. 13, 3513-3528 (2005). Various SS-OCT systems have been reported including systems based on Fourier Domain Mode Locked (FDML) lasers, surface emitting cavity lasers, short cavity lasers, long cavity lasers, and tunable lasers that include a tunable filter.

Some of the implementations disclosed to date suffer from drawbacks that have discourage widespread commercialization of SS-OCT. For example, certain implementations make real-time data acquisition and display difficult, because they employ data acquisition schemes that require post-acquisition re-sampling or interpolation of recorded data before Fourier transformation. In addition, the relatively short coherence length and tendency for mode-hopping of short-cavity lasers reduce signal-to-noise and image resolution at optical scan depths exceeding 2-3 mm. Many medical applications, including coronary artery imaging, require an optical scan depth that exceeds 5 mm. Some OCT system and method implementations designed to address some of the problems outlined above relating to SS-OCT in context of tunable light sources are recited in Schmitt "Method and Apparatus for Swept-Source Optical Coherence Tomography" U.S. Pat. No. 7,916,387 (issued Mar. 29, 2011) and Schmitt "Method and Apparatus for Swept-Source Optical Coherence Tomography" U.S. Pat. No. 8,325,419 (issued Dec. 12, 2012).

Other approaches relating to SS-OCT and the light sources used with such systems have been proposed. For example, SS-OCT systems using a vertical-cavity surface-emitting laser (VCSEL) laser are described in Jayaraman "System for Swept Source Optical Coherence Tomography" U.S. Pat. No. 7,468,997 (issued Dec. 23, 2008) and Chong "Swept Source Type Optical Coherent Tomography System" U.S. Pat. No. 7,701,588 (issued Apr. 20, 2010).

In general, for SS-OCT systems, it is often the case that the swept light sources that are used exhibit nonlinear sweep patterns. As a result, the optical frequency of light generated by the source does not change linearly over each sweep period. These light sources may also suffer from asymmetry in the forward and backward scans. Further, the nonlinearity and asymmetry problems tend to vary from light source to light source, which makes it difficult, if not impossible, to apply the same corrective action to every unit. A need therefore exists to address such problems. In part, the embodiments described herein address these problems and others relating to certain light sources.

SUMMARY

In part, one embodiment of the invention relates to light sources that are responsive to a time varying electrical signal alternatively referred to herein as a drive waveform or drive signal. The light sources can be configured for use with a data collection system and one or more associated data collection probes. The drive waveform can be used to control a swept light source such as by controlling a tunable filter. In one embodiment, the data collection system is an optical coherence tomography ("OCT") system. In part, the invention relates to methods suitable for use with light sources that are in optical communication with or otherwise include a tunable filter that has an asymmetric and/or nonlinear response to a drive waveform.

In one embodiment, a plurality of waveforms, such as sinusoids, are combined to create a waveform suitable for driving a light source or a component thereof such as a tunable filter. In one embodiment, the combination waveform is configured to reduce or correct an asymmetric sweep response and a nonlinear sweep response simultaneously. That is, instead of improving the asymmetric sweep response of the light source while the nonlinear sweep response stays the same or worsens or does not improve to a satisfactory level (or vice versa with respect to improving the nonlinear sweep response while the asymmetric sweep response stays the same or worsens or does not improve to a satisfactory level), both symmetry and linearity of the sweep response of the light source are improved by the drive waveform.

In one embodiment, a filter or light source has or produces a wavelength tuning profile in one sweep direction that is not a mirror image of the profile in the other sweep direction even though a symmetric drive waveform is applied to the filter. This is an example of a type of asymmetric sweep response. For example, application of a sinusoidal drive waveform, which is symmetric in time about a point halfway through its repetition period, may result in a forward sweep that is longer in duration than the backward sweep. In one embodiment, a filter or light source lacks or otherwise does not produce a tuning profile that is linear in optical frequency with time. This is an example of a type of nonlinear sweep response. For example, application of a sinusoidal drive waveform may result in forward and backward sweep profiles that are sinusoidal in optical wavelength with time.

In one embodiment, the light source is a vertical-cavity surface-emitting laser (VCSEL), a FDML light source, or a tunable light source that includes or is in optical communication with a tunable filter. The filter can include a MEMs device in one embodiment. The filter can include a piezoelectric component in one embodiment. In one embodiment, the second harmonic is tuned to correct asymmetry and the third harmonic is tuned to correct nonlinearity in the forward and backward scans. In one embodiment, the second harmonic is tuned to correct nonlinearity and the third harmonic is tuned to correct asymmetry in the forward and backward scans. The tuning can be performed by modifying the second harmonic and the third harmonic by adjusting one or more of their respective phases or amplitudes.

In one aspect, the invention relates to a method of controlling a light source having a tunable filter. The method includes generating a first harmonic wave having a first frequency, wherein the first harmonic wave has a first amplitude indicative of a voltage and a first phase; generating a second harmonic wave having a second frequency, wherein the second harmonic wave has a second amplitude indicative of a voltage and a second phase; generating a third harmonic wave having a third frequency, wherein the third harmonic wave has a third amplitude indicative of a voltage and a third phase; generating a modified second harmonic wave; generating a modified third harmonic wave; and superpositioning the first harmonic wave, the modified second harmonic wave and the modified third harmonic wave to generate a drive waveform configured to substantially symmetrize and substantially linearize a sweep response of the light source.

In one embodiment, the method further includes storing the drive waveform in memory. In one embodiment, the step of generating a modified second harmonic wave includes substituting the second phase with a fourth phase such that the modified second harmonic results; and the step of generating a modified third harmonic wave includes substituting the third phase with a fifth phase such that the modified third harmonic wave results. In one embodiment, the step of generating a modified third harmonic wave includes substituting the third amplitude with a fourth amplitude such that the modified third harmonic wave results. In one embodiment, the method further includes driving the tunable filter with the drive waveform and storing optical coherence data. In one embodiment, the light source is a vertical-cavity surface-emitting laser (VCSEL). In one embodiment, the method further includes increasing an effective duty cycle of the VCSEL to be greater than or equal to 90% of a sweep period of the light source by driving the tunable filter with the drive waveform. In one embodiment, the step of generating a modified second harmonic wave includes substituting the second amplitude with a fifth amplitude such that the modified second harmonic wave results.

In one embodiment, the method further includes adjusting a constant voltage bias of the drive waveform such that a center wavelength of the light source is about 1310 nm. In one embodiment, the method further includes adjusting an alternating current gain of the drive waveform such that a tuning range of the light source is about 100 nm. In one embodiment, configuring the waveform to substantially symmetrize and substantially linearize a sweep response includes the steps of generating a sweep response that has (i) a scan duration in the forward scan direction that differs from a scan duration in the backward scan direction by less than about 15% and (ii) a peak RF frequency in the forward scan direction that differs from a peak RF frequency in the backward scan direction by less than about 15%.

In one aspect, the invention relates to an optical coherence tomography system. The system includes a drive waveform source that includes a memory, an output, and one or more function generators configured to (a) generate a first harmonic wave, (b) generate a second harmonic wave (c) generate a third harmonic wave; and (d) combine the first, second, and third harmonic waves such that a drive waveform is generated and stored in the memory; and a light source that includes a tunable filter, the tunable filter in electrical communication with the output and configured to receive the drive waveform from the output, wherein the second harmonic has a first phase value and/or a first amplitude value configured to cause a peak radiofrequency (RF) OCT signal frequency for a backward scan of the tunable filter and a peak RF OCT signal frequency for a forward scan of the tunable filter to differ by less than about 15%.

In one embodiment, the drive waveform source is a control system, a processor or a circuit. In one embodiment, the light source is a VCSEL. In one embodiment, the light source is an FDML laser or any tunable light source incorporating a filter with an asymmetric or nonlinear response. In one embodiment, wherein the third harmonic has a second phase value and a second amplitude value configured to minimize a peak RF OCT signal frequency for a backward scan and a forward scan. A control system, a processor or a circuit can be used to generate one or more functions such as waveforms and combine them to generate the drive waveforms specified herein.

In one embodiment, the first phase value is generated by searching for an extremum in a two dimensional space that includes forward and backward scan data measured with respect to the light source as the tunable filter is swept. In one embodiment, the first phase amplitude is generated by searching for an extremum in a two dimensional space that includes forward and backward scan data measured with respect to the light source as the tunable filter is swept. In one embodiment, the effective duty cycle of the VCSEL is greater than about 90% of a sweep period of the VCSEL when collecting OCT data.

In one embodiment, the VCSEL has a tuning range of about 100 nm. In one embodiment, a forward scan duration of the tunable filter is about equal to a backward scan duration of the tunable filter. In one embodiment, a ratio of a forward scan duration to a backward scan duration ranges from about 0.8 to about 1.2 when the drive waveform is applied to the tunable filter. In one embodiment, a ratio of a peak RF OCT signal frequency during a forward scan to a peak RF fringe frequency during a backward scan duration ranges from about 0.9 to about 1.1 when the drive waveform is applied to the tunable filter.

In one aspect, the invention relates to a method of controlling an optical coherence tomography system. The optical coherence tomography system includes a light source comprising a tunable filter. The method includes generating a first harmonic wave having a first frequency, wherein the first harmonic wave has a first amplitude indicative of a voltage and a first phase; generating a second harmonic wave having a second frequency, wherein the second harmonic wave has a second amplitude indicative of a voltage and a second phase; generating a third harmonic wave having a third frequency, wherein the third harmonic wave has a third amplitude indicative of a voltage and a third phase; generating a modified second harmonic wave; generating a modified third harmonic wave; superpositioning the first harmonic wave, the modified second harmonic wave and the modified third harmonic wave to generate a drive waveform; and generating a sweep response for the light source comprising a scan duration in a forward scan direction that differs from a scan duration in a backward scan direction by less than about 15% by driving the tunable filter with the drive waveform.

In one aspect, the invention relates to an optical coherence tomography system. The system includes a swept light source that includes a tunable filter that includes an input, the tunable filter in optical communication with a sample arm of an interferometer, wherein the tunable filter is drivable bidirectionally; a control system that includes a non-transitory memory and an output, wherein the output is in electrical communication with the input, the control system configured to drive the tunable filter in one or more directions; and a drive waveform stored in the non-transitory memory, the drive waveform configured to substantially symmetrize and substantially linearize a sweep response of the swept light source, wherein an effective duty cycle of the swept light source is greater than about 90% of a sweep period of the swept light source when collecting optical coherence tomography data.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

FIG. 3A shows a plot of drive amplitude versus time with respect to a drive waveform according to an illustrative embodiment of the invention.

FIG. 3B shows a plot of measured signal frequency versus time with respect to a drive waveform according to an illustrative embodiment of the invention.

DETAILED DESCRIPTION

In part, the invention relates to methods, systems and devices for determining a suitable drive waveform for use with an electromagnetic radiation source alternatively referred to herein as a light source such that the drive waveform improves one or more operational parameters of the light source. In one embodiment, the light source is a swept source such as a swept source laser. The light source is typically configured for use with a data collection system such as an OCT system. In one embodiment, the light source is a VCSEL, a Fourier Domain Mode Locked laser, or a light source incorporating a tunable filter with an asymmetric response, a nonlinear response or both an asymmetric and non-linear response. In one embodiment, the tunable filter is drivable bidirectionally.

Figure 1A:
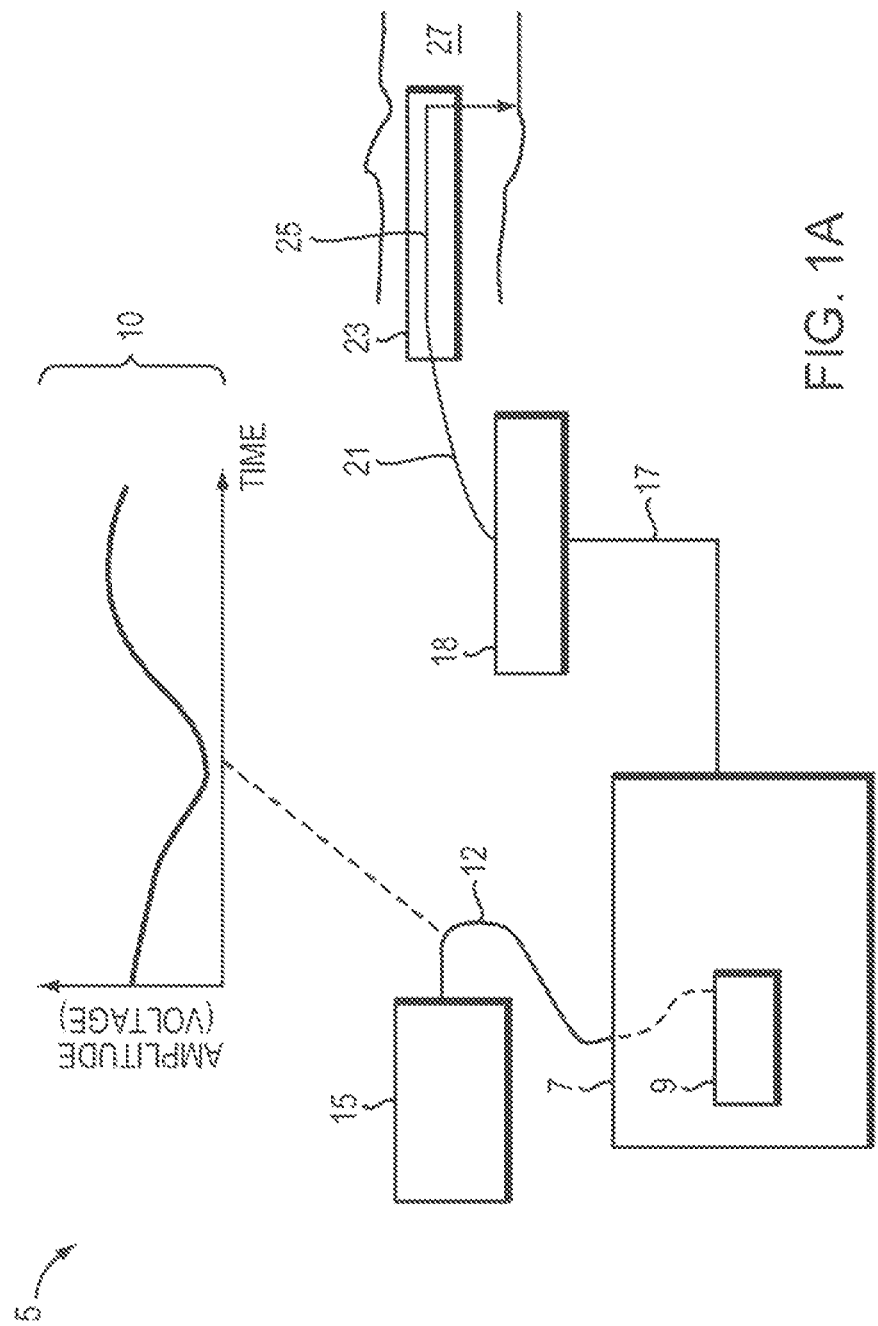
FIG. 1A shows an optical coherence tomography system with a light source driven by a drive waveform according to an illustrative embodiment of the invention.

Intravascular OCT imaging systems, such as the system 5 of FIG. 1A, include a light source 7 such as a wavelength-swept light source. In one embodiment, the light source includes or is in optical communication with a tunable filter 9. The tunable filter 9 can be a device such as a MEMs device that it is in optical communication with the light source 7. The tunable filter 9 can be a component of the light source 7. Swept light sources, such as source 7, generally produce alternating series of "forward" (short to long wavelength) and "backward" (long to short wavelength) scans as a tunable filter 9 of the light source 7 is driven with a drive waveform 10. In one embodiment, the drive waveform 10 is an oscillating, periodic drive waveform such as a sinusoidal voltage waveform.

As discussed in more detail below, the drive waveform 10 can be configured to increase the effective duty cycle of the light source 7. In one embodiment, effective duty cycle refers to the percentage of time during the period of the drive waveform where OCT image data can be collected. The effective duty cycle can vary based on the quality of the laser output, the RF OCT signal frequency, and the sampling rate of the OCT digitizer system. In addition, the drive waveform 10 can include a plurality of component waves used to generate a resultant waveform such as by Fourier synthesis. In one embodiment, the drive waveform 10 includes three component waves that are selected such that when combined symmetry and linearity of the output light source 7 are improved relative to other types of input waveforms. The drive waveform 10 can be used to control light source 7 or a component in optical communication with the light source 7.

Certain swept light sources that are suitable for use in OCT systems suffer from inherently nonlinear sweep patterns, whereby the optical frequency of light generated by the source, such as source 7, does not increase or decrease linearly over each sweep period. Furthermore, these light sources may also suffer from inherent asymmetry in the forward and backward scans, whereby the scan produced in one direction may be compressed or distorted compared to the other direction due to the properties of the tunable filter used in the light source. Since the tunable filter, such as filter 9, used in each individual light source has unique response characteristics, the nature of the nonlinearity and asymmetry problems can vary from unit to unit, making it impossible to apply the same corrective action to every unit. As a result, drive waveforms 10 can be designed on a per light source basis to improve the operation of a given light source in a given OCT system. A drive waveform source 15 can include a processor, one or more function generators, a non-transitory memory, a suitable control system or other suitable electronic devices configured for generating and configuring drive waveforms for transmission to the tunable filter 9.

In one embodiment, the drive waveform source 15 is a control system that includes a non-transitory memory and an output such as a port or contact. The tunable filter can be in optical communication with a sample arm of an interferometer in one embodiment. The tunable filter can include an input such as port or a contact configured to receive a control signal such as a drive waveform 10. The tunable filter is drivable bidirectionally. Although, in some embodiments, the drive waveform 10 can be used to drive the tunable filter in one direction. The drive waveform 10 can also be used to drive the tunable filter in one or more directions. In one embodiment, the output is in electrical communication with the input. The drive waveform can be generated for a particular light source and stored in the non-transitory memory or created by the waveform source and stored in a non-transitory memory. In one embodiment, the drive waveform is configured to substantially symmetrize and substantially linearize a sweep response of the swept light source. In one embodiment, the effective duty cycle of the swept light source is greater than about 90% of a sweep period of the swept light source when collecting optical coherence tomography data.

A drive waveform 10 that includes a plurality of related or harmonic sine waves configured to correct and/or improve upon both the nonlinearity and asymmetry found in certain swept light sources 7 and methods of determining such as drive waveform are both embodiments of the invention. An OCT system with such a drive waveform or drive waveform source 15 is also one embodiment of the invention. In other embodiments, a stepwise method for determining the relative weighting and phase offsets of the constituent sine waves is used such that an optimal waveform can be selected for an individual light source.

As shown in FIG. 1A, the OCT system 5 includes a light source 7, such as a wavelength swept light source, which can include a tunable filter 9. A drive waveform is determined based on one or more parameters of the light source 7. Typically, a plurality of parameters are evaluated, such as phase, amplitude, sweep duration, peak RF OCT signal frequency, and other scan direction specific parameters, as part of the process of determining a suitable drive waveform 10. In one embodiment, two parameters are evaluated simultaneously to improve linearity and symmetry of the sweep response. The drive waveform 10 is transmitted to the light source 7 through an electrical connection 12 such as one or more wires, a bus, or other data transmission mechanism, in one embodiment. The waveform source 15 is in electrical communication with light source 7, such as for example, by being in electrical communication with a tunable filter 9. If the swept source 7 does not include a tunable filter, the drive waveform source 15 can be in electrical communication with another component of the light source 7 having an input configured to receiving a drive waveform 10.

In one embodiment, the light source 7 is in optical communication with an interferometer 18. As shown, an optical path 17 such as one or more optical fibers can be used to facilitate optical communication between the light source 7 and the interferometer 17. The interferometer may be a Michelson interferometer. A probe 23 such as an OCT data collection probe can be in optical communication with interferometer 18 along another optical path 21 such as another optical fiber as shown. In one embodiment, the probe includes a rotatable fiber 25 disposed within a catheter. The rotatable fiber 25 can be in optical communication with optical path 21. The probe 23 can be sized for insertion into a sample 27 or lumen of interest, such as a blood vessel or artery. In one embodiment, the probe 25 receives electromagnetic radiation directed from the light source 7 to the interferometer 18. The probe in turn directs light into a sample 27, such as a blood vessel, and collects reflected light from the blood vessel. The interferometer 18 is used in accordance with OCT principles to generate depth information based on the light from the source 7 and the light collected from the sample 27.

Figure 2:
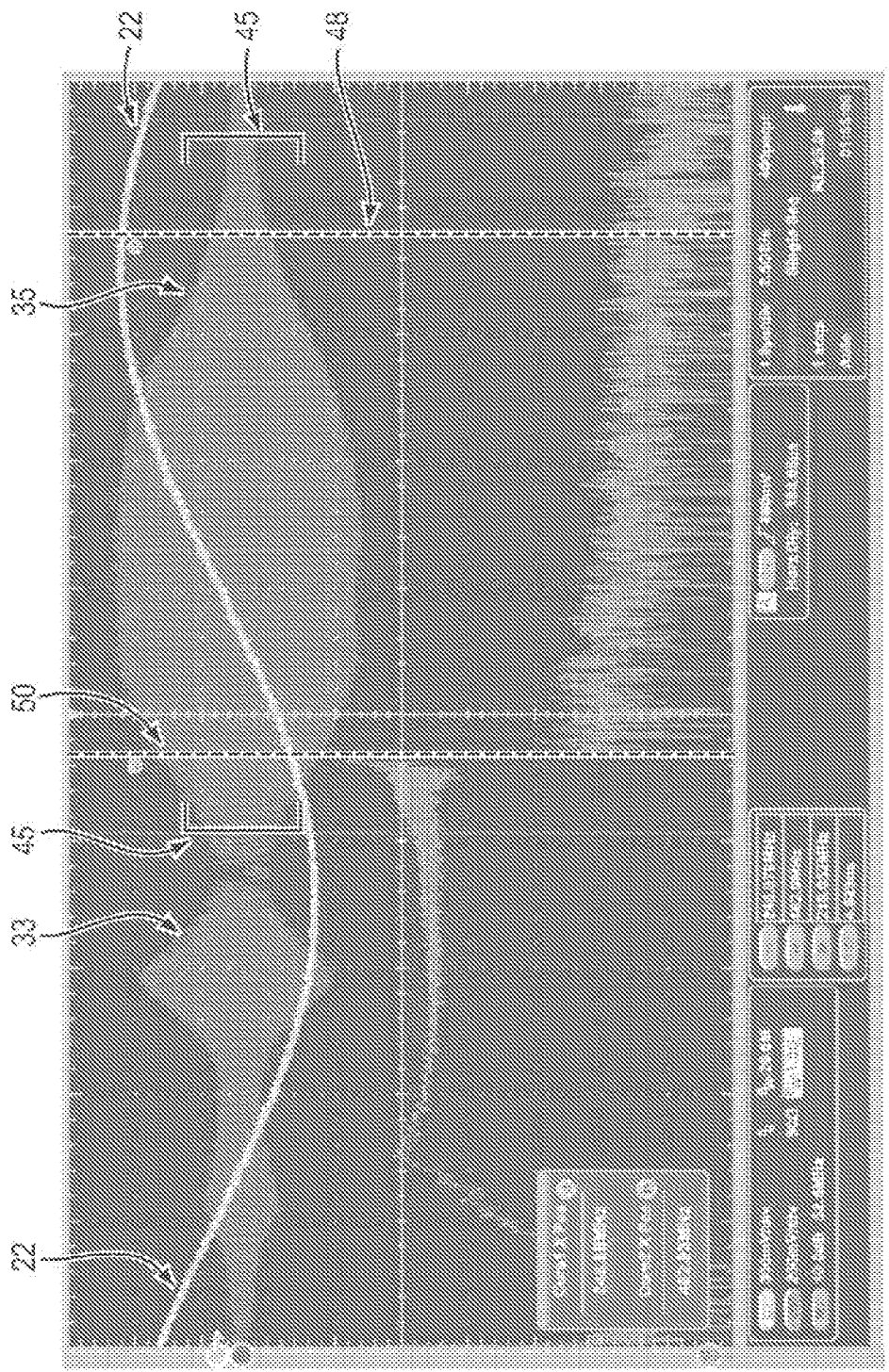
FIG. 2 shows an oscilloscope screenshot depicting various parameters of a drive waveform that includes a fundamental wave in accordance with an illustrative embodiment of the invention.
Figure 5:
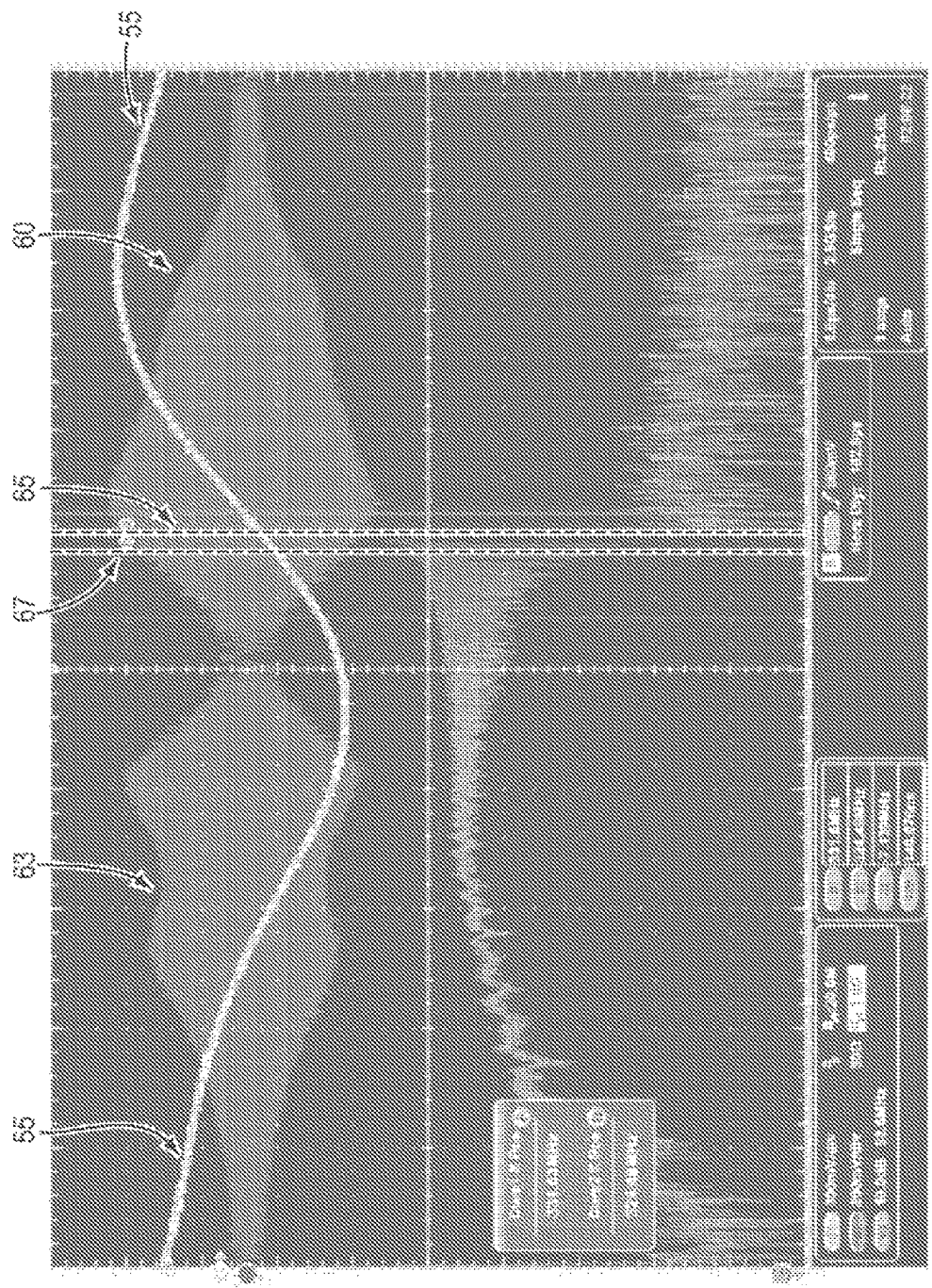
FIG. 5 shows an oscilloscope screenshot depicting various parameters of a drive waveform that includes a second harmonic wave in accordance with an illustrative embodiment of the invention.
Figure 7:
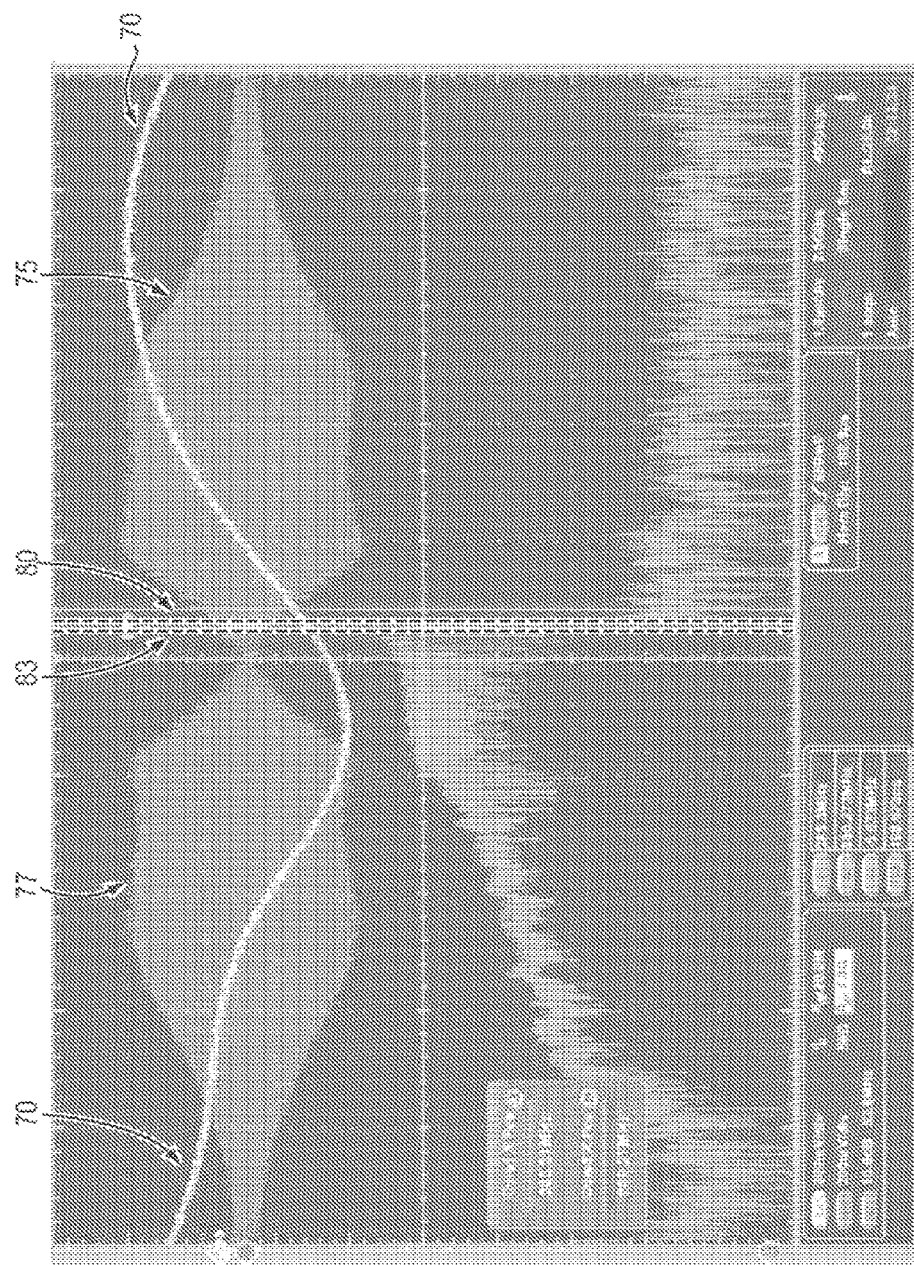
FIG. 7 shows an oscilloscope screenshot depicting various parameters of a drive waveform that includes a third harmonic wave in accordance with an illustrative embodiment of the invention.

A drive waveform source 15 such as a control system can be used to generate a suitable drive waveform to control the tunable filter 9 and/or the light source 7 in one embodiment. The output response of a light source 7 for different input drive waveforms 22, 55, 70, respectively, are shown in FIGS. 2, 5, and 7. The waveform can be synthesized by combining the outputs of three sine wave generators. Alternatively, an arbitrary waveform generator can be used to directly synthesize the waveform. In either case, in one embodiment, a general formula for the waveform $f(t) = V_{DC} + A_0 \sin(2\pi f_0 t + \Phi_0) + A_1 \sin(2\pi f_1 t + \Phi_1) + A_2 \sin(2\pi f_2 t + \Phi_2)$, where $V_{DC}$ is a DC bias voltage, $f_2 = 3f_0$ and $f_1 = 2f_0$. For example, $A_0$ can range from between about 0 V to about 200 V, $f_0$ can range from about 25 kHz to about 2 MHz.

The various function generators described herein such as sine wave generators can be implemented using circuits, devices, and software modules. The various function generators can be part of the drive waveform source 15 or in electrical or optical or wireless communication with it. The drive waveform source 15 can include a processor such as a central processing unit or a microprocessor or an ASIC with instructions to generate a suitable drive waveform Alternatively, the drive waveform source can include or be able to access memory that includes a previously generated and stored waveform suitable for a given light source or tunable filter. The invention is not limited to the use of sine wave generators or sine waves, but can be implemented using various drive wave forms generated by combining harmonic functions, non-harmonic functions, and other functions in various embodiments to provide a suitable drive waveform as outlined herein.

In one embodiment, the light source 7 is a tunable laser that includes or is in optical communication with a tunable filter. In part, one embodiment of the invention relates to a method to derive a drive waveform suitable for use with a light source 7 such that a suitable level of symmetry and/or linearity or an increased duty cycle results such as an optimized level or maximum level. Three harmonic waves, such as sinusoids or sine waves, are combined to generate the drive waveform in one embodiment. In one embodiment, the fundamental frequency of the first wave (the first harmonic) is about 100 KHz. The frequencies of the second wave (second harmonic) and third wave (third harmonic) can be integer multiples of the fundamental frequency of the first wave. In one embodiment, the frequency of the second wave is about 200 kHz. In one embodiment, the frequency of the third wave is about 300 kHz.

Figure 1B:
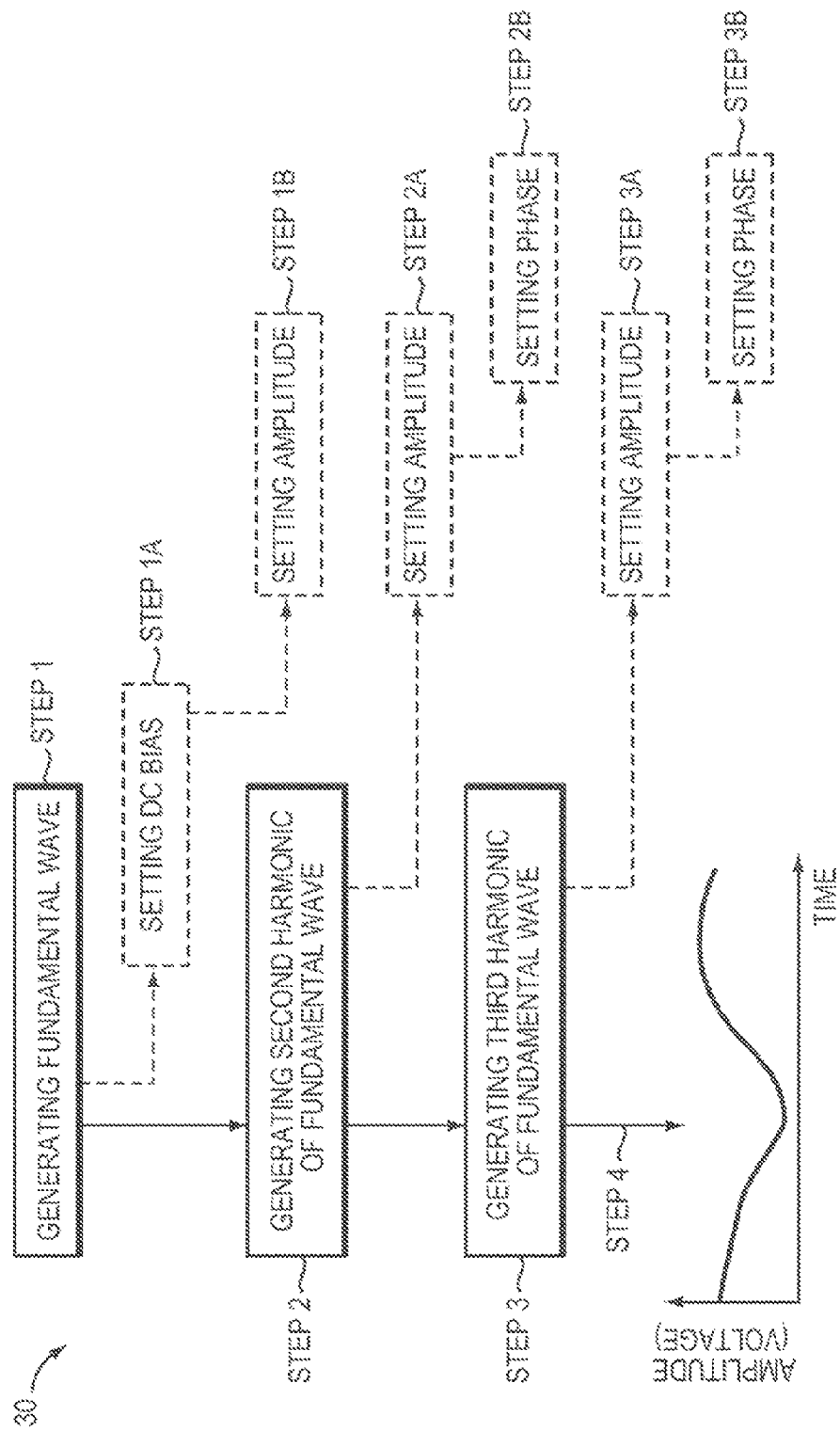
FIG. 1B shows a method of designing and/or generating a drive waveform suitable for use with a light source in an optical coherence tomography system in accordance with an illustrative embodiment of the invention.

A suitable drive waveform configured for use with a light source such as a laser can be designed or generated on a per light source basis. One method 30 for generating such a drive waveform is shown in FIG. 1B. Initially, the first step is generating the fundamental sine wave Step 1. In addition, another step, which may be optional in some embodiments, is setting the constant voltage bias Step 1a to obtain a desired center wavelength of the wavelength sweep. Another step, which may be optional in some embodiments, is setting the amplitude of fundamental sine wave Step 1b to obtain a desired tuning range. These steps may be performed iteratively until a target DC bias and/or target amplitude is reached that yield an optimal or otherwise suitable drive waveform. The next step is generating the second harmonic Step 2.

In one embodiment, the amplitude of the second harmonic is adjusted as well as its phase. As a result, additional steps can include setting the amplitude of the second harmonic Step 2a and setting the phase of the second harmonic Step 2b to substantially symmetrize the forward scan and the backward scan with respect to time and frequency or to obtain maximum time and frequency symmetry between forward and backward scans. The forward and backward scans of the light source are discussed in more detail below. The next step is generating the third harmonic Step 3. Additional steps can include setting the amplitude of the third harmonic Step 3a and setting the phase of the third harmonic Step 3b to substantially linearize the scan or obtain a suitable level of scan linearity. The final step shown is to output a drive waveform Step 4 as shown.

The steps shown in FIG. 1B and otherwise described herein can be performed in different orders with all, some or none of Steps 1a, 1b, 2a, 2b, 3a, and 3b. For example, in one embodiment the second harmonic can be configured to substantially linearize the light source scan while the third harmonic can be configured to substantially symmetrize the light source scan. Additionally, some or all of the steps may be repeated iteratively in order to optimize the light source scan. Adjustments to the amplitude and phase of the various harmonics can be used to configure the waveform to improve certain aspects of the sweep response such as its symmetry and linearity.

FIG. 2 is an oscilloscope screenshot showing various waves and related frequency data associated with a VCSEL light source. FIG. 5 and FIG. 7 show additional oscilloscope screenshots with different drive waveforms. The drive waveforms in FIGS. 5 and 7 include waveform 22 with the second harmonic added (FIG. 5) and the third harmonic added to waveform 22 and the second harmonic (FIG. 7), respectively, or modified versions thereof. The drive waveform 55 of FIG. 5 and the drive waveform 70 of FIG. 7 are suitable for driving a VCSEL light source or a component thereof.

The VCSEL light source includes a tunable filter. The top half of the screenshot of FIG. 2 shows the RF OCT signals, commonly referred to as interference fringes 33 and 35, generated by a Mach-Zehnder interferometer (MZI) when a forward and backward wavelength scan from a VCSEL is used as the interferometer input. The path length difference between the two arms of the MZI was set to about 16.0 mm in air. With this arrangement, the MZI generates interference signals that approximate the signals which would be generated during OTF imaging with a Michelson interferometer at an imaging range of about 8.0 mm in air, which is a desirable range for imaging of blood vessels. In this case, the drive waveform 22 comprises a DC bias voltage and a pure sinusoid with a frequency of 100 kHz and is configured to generate a tuning range of about 100 nm centered near a wavelength of about 1310 nm. The interference fringe amplitude 33 during the backward scan is attenuated compared to the forward scan in part because the RF signal frequency exceeds the bandwidth of the detector electronics.

From the screenshot, it is clear that the VCSEL response is highly asymmetric at 100 kHz drive frequency. The drive waveform 22 corresponds to a sine wave as the fundamental waveform or first harmonic. This fundamental waveform is a time varying voltage as shown and is used to drive a tunable filter used in the VCSEL. In the top half of FIG. 2, the MZI output generated by the VCSEL in response to the input drive waveform 22 is shown. The amplitude along the vertical axis is in units of about 200 millivolts per unit division and time is shown along the horizontal axis in units of 1 microsecond per unit division.

Optical devices such as tunable filters can be driven with a raised cosine waveform. See *Spectrum of Externally Modulated Optical Signals, Ho and Kahn*. Journal of Lightwave Technology, Vol. 22, No. 2, February 2004. Such a drive waveform can include a rapid "flyback" section and an elongated raised cosine section. Under this tunable filter drive condition, the flyback section is intentionally not useable for OCT imaging. Instead, a raised cosine drive waveform attempts to minimize the duration of the flyback while maximizing the duration and linearity of the forward scan. Unfortunately the raised cosine method does not achieve these goals for certain VCSEL designs when the drive waveform frequency is 100 kHz, which is a desirable frequency for operation OCT system. The methods, systems, and device described herein relating to drive waveform design and generation using multiple harmonic sinusoids addresses these limitations of the raised cosine waveform.

As discussed above with respect to FIG. 1A, swept light sources, such as the VCSEL produce alternating series of "forward" (short to long wavelength) and "backward" (long to short wavelength) scans as the tunable filter is driven with a drive waveform. In FIG. 2, the interference fringes from a "backward" scan 33 is shown on the left in the top half of the figure while the "forward" scan 35 is shown on the right side. As discussed herein, the backward scan 33 shown also corresponds to the flyback portion of the VCSEL response to an input drive waveform. The tunable filter used in the VCSEL has a highly nonlinear and asymmetric voltage response when driven at frequencies around 100 kHz. A frequency spectrum is shown in the bottom half of the figure and below waveform 22. The units for the frequency data in the bottom portion of FIGS. 2, 5 and 7 use decibels for the vertical axis and frequency for the horizontal axis.

As shown in the oscilloscope screenshot of FIG. 2 (and in FIGS. 5 and 7) the bottom portion of each screenshot generally shows a radiofrequency spectra generated using a rectangular Fast Fourier Transform (FFT) window sized to 90% of the duration of a single sweep direction (i.e., a forward direction or a backward direction). In FIG. 2, the windowed FFT of forward scan 35 is shown as indicated by brackets 45. In addition, a frequency marker shown as a dotted line 48 corresponds to the peak radiofrequency of the backward scan. This marker 48 shows the highest frequency of the compressed backward scan, 462.9 MHz, which includes an excessive amount of radiofrequencies due to the highly time-compressed nature of the backward scan.

Another marker 50 associated with the forward scan identifies a peak frequency value of 246.88 MHz. It is desirable to have the frequency content of the forward scan and the backward scan to be the same. It is also desirable to minimize the peak frequency contained in the interference fringes generated during OCT imaging. If the frequency content of the two scans is significantly different, data acquisition is more complicated and a more complex data acquisition (DAQ) device is required. Additionally, a higher peak signal frequency necessitates a faster data acquisition device to accurately sample the data, which increases the system cost and complexity.

In FIG. 2, the frequency content differs significantly, as is clear from markers 48, 50, while in FIG. 7 it is more closely matched between the forward and backward scan as a result of the application of a suitably configured drive waveform. In addition, the peak signal frequency generated during the entire sweep period that includes a forward and backward scan is substantially reduced. Using the drive waveform of FIG. 2 would likely necessitate using a more expensive and complex DAQ relative to the drive waveform of FIG. 7. For example, it may be necessary to use a 1 GS/s digitizer in order to sample the OCT signals generated at an imaging depth of about 8.0 mm. By using harmonics of a drive waveform, a better operating range for acquiring data is possible. The oscilloscope screens shots of FIGS. 2, 5 and 7 are obtained with a Mach-Zehnder interferometer (MZI) mismatch equivalent to about 8.0 mm imaging range.

FIG. 3A shows a plot of a 100 kHz sinusoidal drive waveform. The forward (FWD) scan and the backward (BWD) scan portions are identified. The vertical axis is for the drive amplitude and the horizontal axis is for time. The normalized alternating current (AC) component of the drive waveform is shown in the plot of FIG. 3A. The AC gain and DC bias were adjusted to obtain a tuning range of about 100 nm centered near about 1310 rm.

FIG. 3B shows the measured instantaneous interference fringe frequency using the drive waveform of FIGS. 3A and 2 applied to a VCSEL. The VCSEL is part of an OCT system that generates interference fringes as part of the interferometric measurements. The fringe frequency is directly proportional to the location of a sample in a sample arm of an interferometer relative to the location of a reference reflector in a reference arm of an interferometer. An MZI with a fixed path mismatch of about 16.0 mm in air was used to generate the interference fringes, corresponding to an OCT imaging range of about 8.0 mm in air. In one embodiment, a light source comprising a tunable filter is in optical communication with an interferometer having a sample arm and a reference. The light source is configured as described herein with regard to one or more of a duty cycle, a sweep period, a response or other parameters described herein such that the light source is suitable for performing swept source OCT data collection. The light source or a component thereof can be connected to a control system or clocking system in one embodiment.

As shown in FIG. 3B, the forward and backwards scans are highly asymmetric. The vertical axis measures fringe frequency and the horizontal axis measures time. The duration of the forward scan of about 6.25 microseconds is longer than backward scan duration of about 3.75 microseconds. As a result, the ratio of the duration of the forward scan to the backward scan is about 6.25/3.75 or about 1.67. In turn, the peak radiofrequency of the forward scan of about 244 MHz is less than the peak radiofrequency of the backward scan of about 461 MHz. As a result, the ratio of the peak radiofrequency of the forward scan to the peak radiofrequency of the backward scan is about 244 MHz/461 MHz or about 0.529.

FIG. 3B also shows a DAQ Cutoff line corresponding to the maximum fringe frequency of 275 MHz that can be sampled by a DAQ system incorporating a 550 megasample/second digitizer. The backward scan exceeds the DAQ Cutoff, making it unusable for OCT imaging with this digitizer. The forward scan is below the DAQ Cutoff, making it usable for OCT imaging with this digitizer. Since only one scan direction is usable, the effective line rate of the OCT system would be 100 kHz and the effective duty cycle would be about 62.5%. FIG. 3B also shows an ideal line corresponding to the fringe frequency that would be obtained with a perfectly linear and symmetric wavelength sweep. The backward scan deviates substantially from this best-case situation.

Figure 3C:
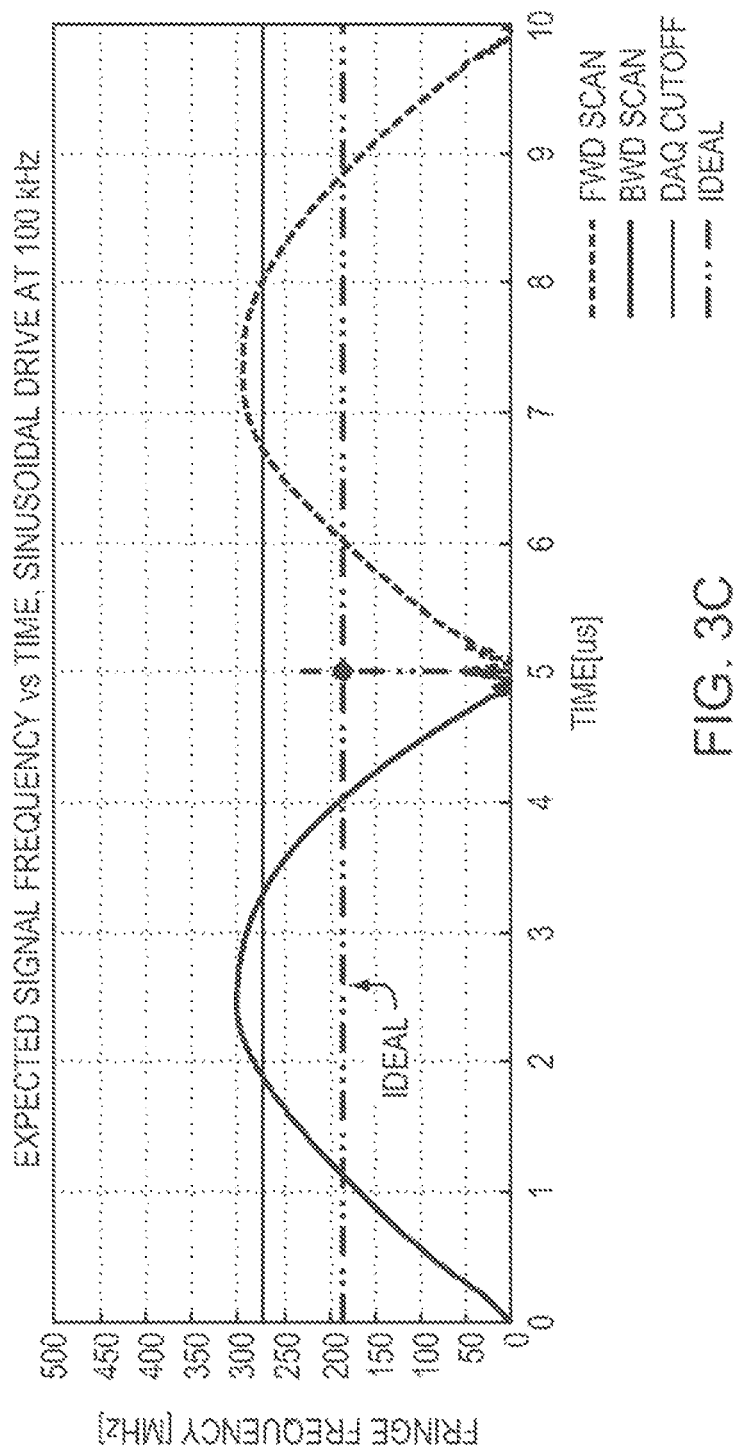
FIG. 3C shows a plot of expected signal frequency versus time with respect to a drive waveform according to an illustrative embodiment of the invention.

FIG. 3C shows the expected instantaneous frequency given the 100 kHz applied drive waveform of FIG. 2 and FIG. 3A. The nonlinear VCSEL response yields a significantly different frequency profile compared to expectation from the applied drive waveform. The plots of FIGS. 3B and 3C demonstrate the need to find a suitable drive waveform to overcome these issues. As described with respect to FIG. 1B, using harmonics of the 100 kHz fundamental wave to tailor a drive waveform allows for many of these negative features to be improved upon or corrected.

Figures 4A, 4B:
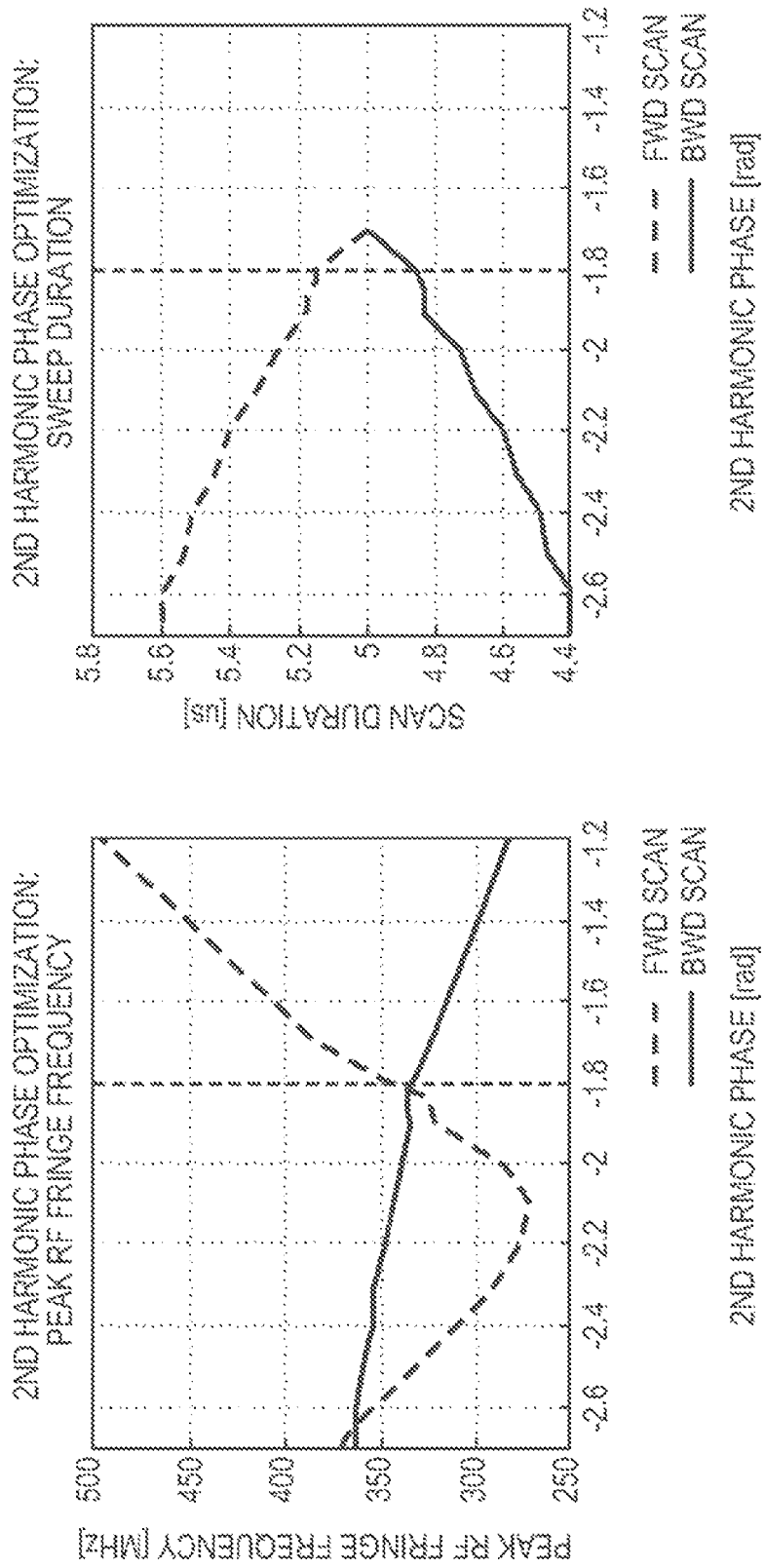
FIG. 4A shows a plot of the peak RF fringe frequency versus phase of a drive waveform that includes a second harmonic according to an illustrative embodiment of the invention.
FIG. 4B shows a plot of the sweep scan duration versus phase of a drive waveform that includes a second harmonic according to an illustrative embodiment of the invention.

Given the limitations associated with using a sine wave as a drive waveform without further modifications, it is useful to add a second harmonic to the fundamental harmonic. In addition, it is also useful to modify the second harmonic by changing its amplitude and phase. FIG. 4A shows the phase optimization of the second harmonic with respect to peak RF frequency. FIG. 4B shows the phase optimization of the second harmonic with respect to sweep scan duration. Phase is measured in radians as shown. Each of FIGS. 4A and 4B define a respective two dimensional (2D) space or a combination 2D space.

The second harmonic (200 kHz) wave, such as a sine wave, is used to substantially symmetrize forward and backward scans. One or more 2D spaces of amplitude and phase are searched to a find point of maximum symmetry, such as a relative maximum or extremum or an absolute maximum or extremum for one or more parameters. In one embodiment, analysis and searching of data sets, such as 2D data sets corresponding to FIGS. 4A and 4B, using maximum or extermum identifying techniques identified about −1.83 radians as suitable phase selection for the second harmonic. A phase value of about −1.83 radians is suitable for use with the second harmonic because the peak RF frequency and the sweep scan duration are both close to equal with this phase value. Thus, a second harmonic can undergo a phase adjustment to generate a modified second harmonic. In one embodiment, the process of identifying an optimal second harmonic amplitude and phase is automated by searching the 2D space for the point of maximum symmetry. Automation can be achieved through computer-controlled waveform generation and frequency measurements. The search may be exhaustive within defined limits of amplitude and phase, or may incorporate conventional search optimization algorithms well-known in the art.

FIG. 5 is an oscilloscope screenshot showing various waves and related frequency data associated with a VCSEL light source. The drive waveform 55 shown in FIG. 5 includes the waveform 22 of FIG. 2 with a second harmonic thereof added to it after the second harmonic is optimized as discussed above with respect to FIGS. 4A and 4B. The forward scan duration 60 and the backward scan duration 63 are substantially identical. The frequency marker at peak RF of backward scan 65 has a frequency of about 331.63 MHz. Similarly, the frequency marker at peak RF of forward scan 67 has a frequency of about 324.49 MHz. From the shape of the uppermost scans and these measurements, there are nearly identical peak RF frequencies and scan durations which result after optimization of the second harmonic's amplitude and phase. As a result, the ratio of the peak radiofrequency of the forward scan to the peak radiofrequency of the backward scan is about 324.49 MHz/331.63 MHz or about 0.978.

Figure 6A:
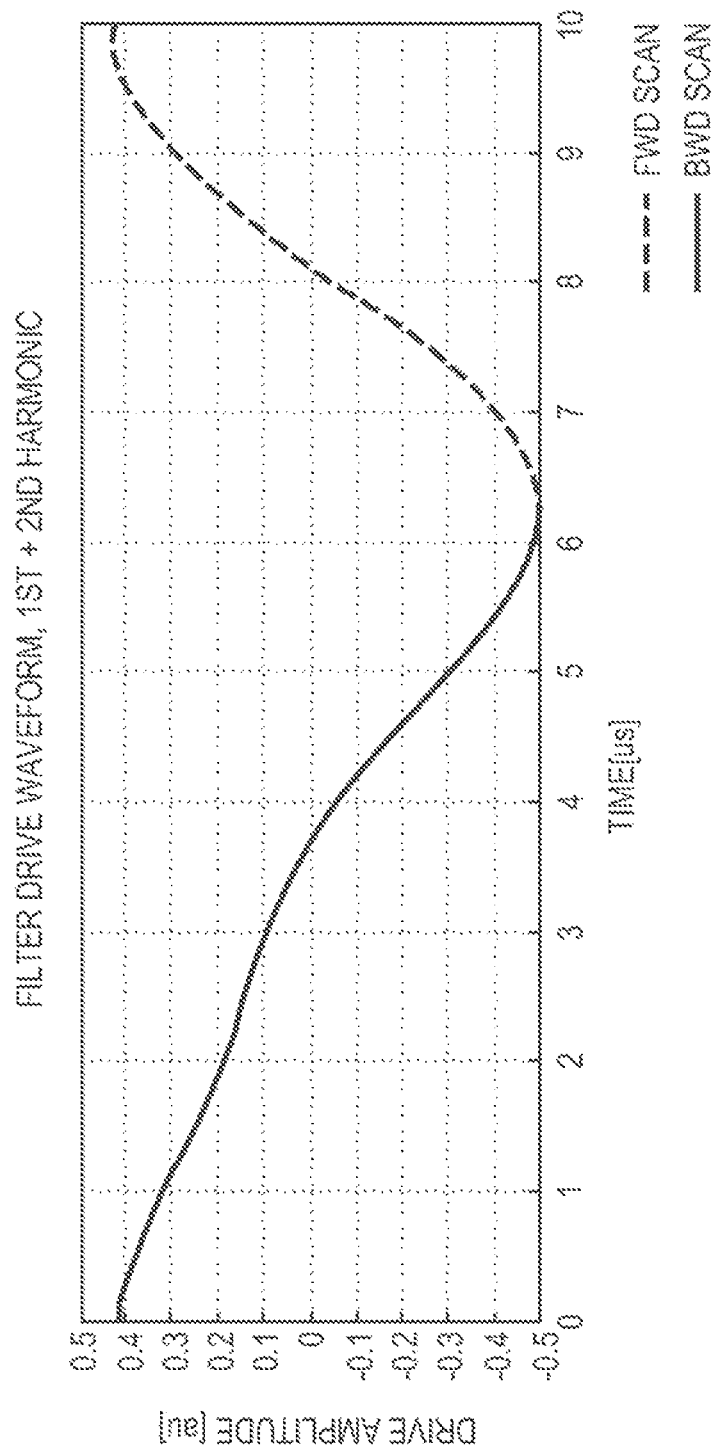
FIG. 6A shows a plot of drive amplitude versus time with respect to a drive waveform composed of two harmonics according to an illustrative embodiment of the invention.

FIG. 6A shows a plot of a sinusoidal drive waveform that includes the second harmonic drive waveform of FIG. 5 and the fundamental harmonic drive waveform of FIG. 2. The forward (FWD) scan and the backward scan portions are identified. The vertical axis is for the drive amplitude and the horizontal axis is for time. The normalized alternating current (AC) component of the drive waveform is shown in the plot of FIG. 6A. The AC gain and DC bias were readjusted to obtain a tuning range of about 100 nm centered near about 1310 nm.

Figure 6B:
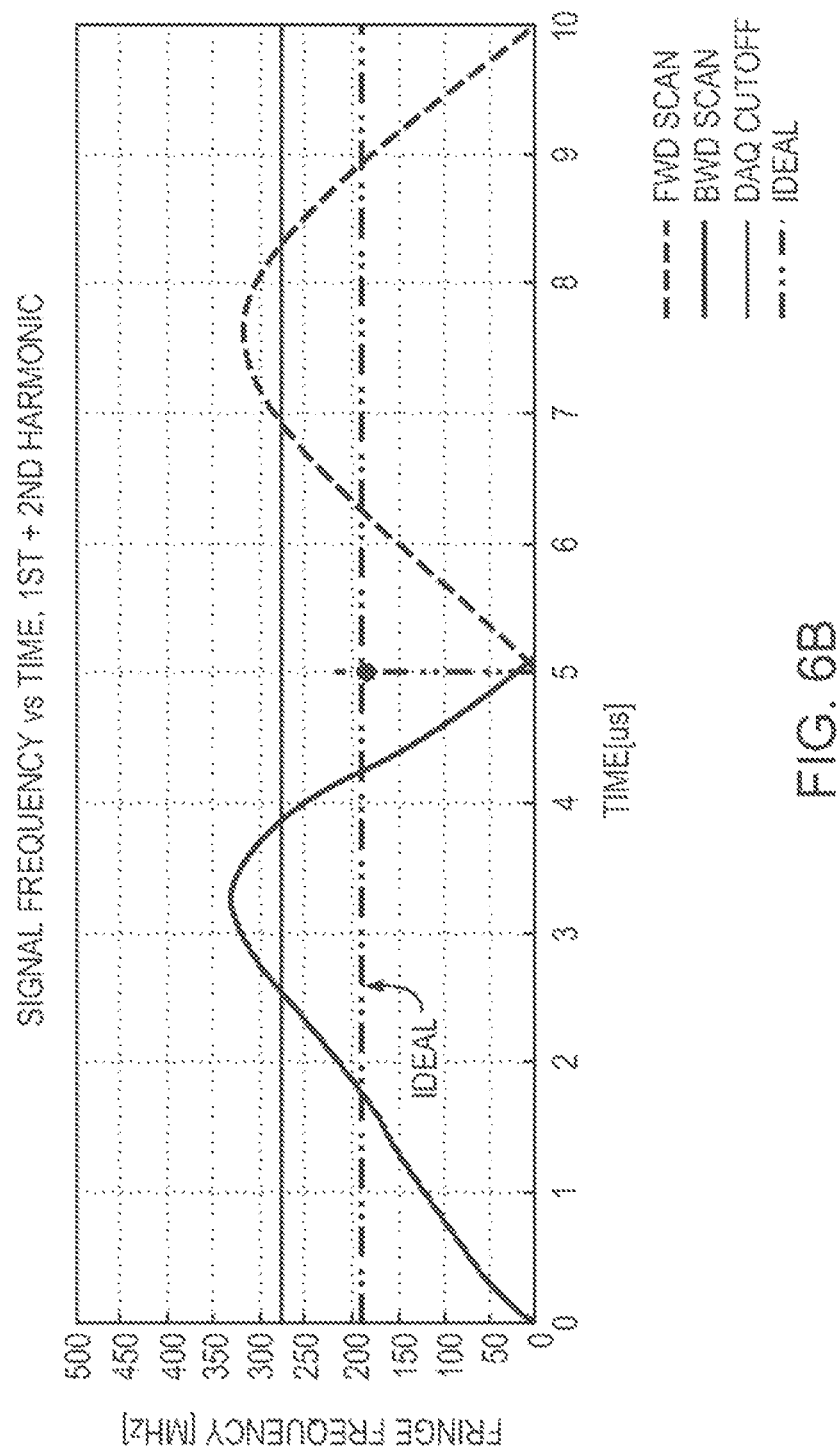
FIG. 6B shows a plot of measured signal frequency versus time with respect to a drive waveform according to an illustrative embodiment of the invention.

FIG. 6B shows the measured instantaneous frequency using the drive waveform of FIGS. 6A and S applied to a VCSEL. As shown, the forward and backwards scans are highly symmetric. The vertical axis measures fringe frequency and the horizontal axis measures time. The duration of the forward scan of about 5.16 microseconds is slightly longer the backward scan duration of about 4.84 microseconds. The ratio of the forward scan duration to the backward scan duration is about 1.157. In turn, the peak radiofrequency of the forward scan of about 320 MHz is only slightly less than the peak radiofrequency of the backward scan of about 327 MHz. The ratio of these two frequency (forward/backward) is about 0.979. In addition, the forward scan and the backward scan are both approaching the DAQ cutoff which would result in a useable line rate of 200 kHz and an effective duty cycle of about 100%. The next step to modify the drive waveform of FIG. 5 is to add a third harmonic to further increase its suitability for use with a given light source for an OCT system.

Figure 6D:
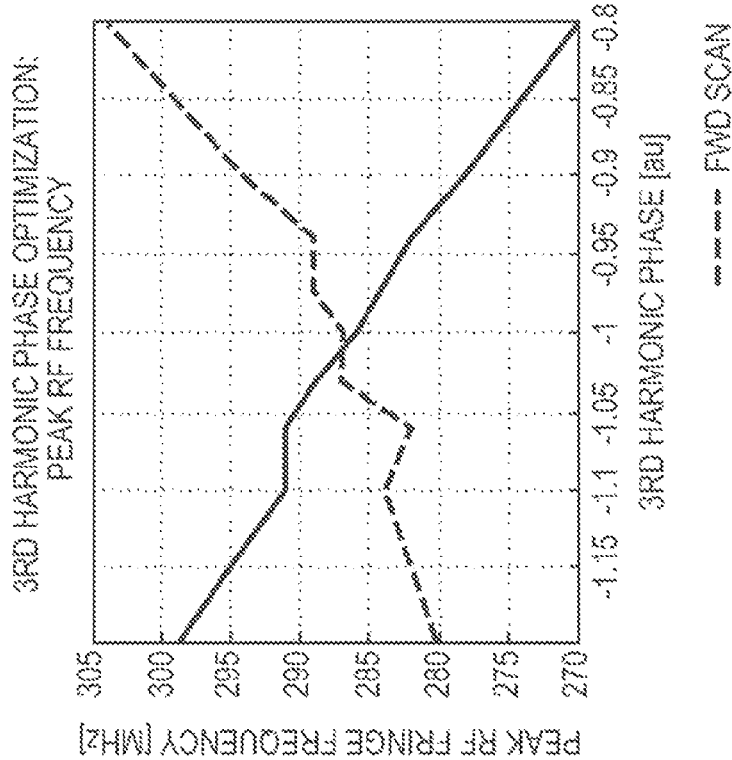
FIG. 6D shows a plot of the peak RF fringe frequency versus phase of a drive waveform that includes a third harmonic according to an illustrative embodiment of the invention.
Figure 6C:
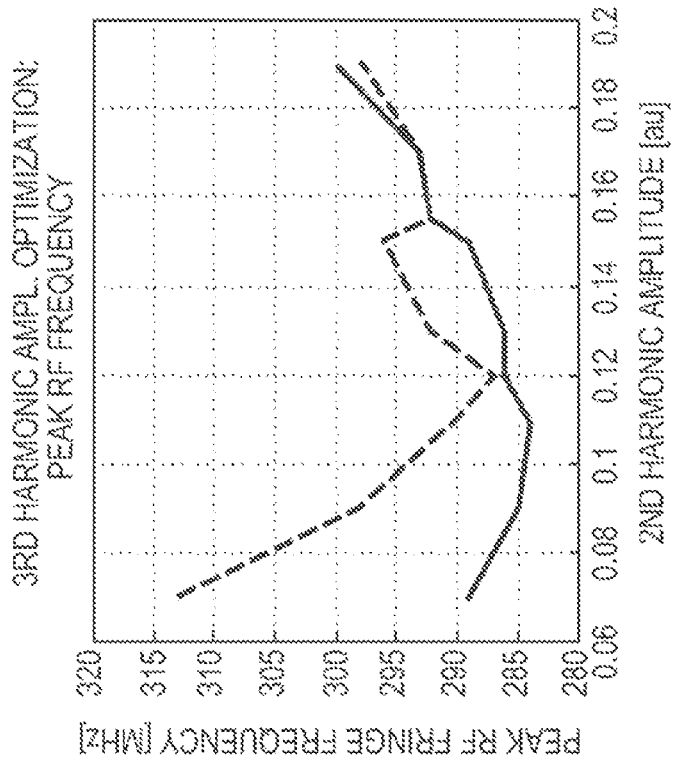
FIG. 6C shows a plot of the peak RF fringe frequency versus amplitude of a drive waveform that includes a third harmonic according to an illustrative embodiment of the invention.

FIG. 6C shows the amplitude optimization of the third harmonic with respect to peak RF frequency. FIG. 6D shows the phase optimization of the third harmonic with respect to peak RF frequency. Phase is measured in radians as shown. Each of FIGS. 6C and 6D defines a respective two dimensional (2D) space or a combination 2D space. The third harmonic (300 kHz) wave, such as a sine wave, is used to substantially linearize the forward and backward scans. One or more 2D spaces of amplitude and phase are searched to a find point of minimum RF frequency, such as a relative minimum or extremum or an absolute minimum or extremum for one or more parameters.

In one embodiment, analysis and searching of data sets, such as 2D data sets corresponding to FIGS. 6C and 6D, using maximum or extermum identifying techniques identified an amplitude of about 0.12 and a phase of about −1.01 radians. This amplitude and phase were identified because the peak RF frequency is substantially minimized with these values of amplitude and phase. These values substantially linearize the response of a given light source such as a tunable laser, for example, when the drive waveform includes the fundamental wave, the second harmonic, and the third harmonic with the parameters described herein or variations in such parameters as is possible with one or more of the optimization steps.

FIG. 7 is an oscilloscope screenshot showing various waves and related frequency data associated with a VCSEL light source. The drive waveform 70 shown in FIG. 7 includes the waveform 55 of FIG. 5 added to the third harmonic after it is optimized as discussed above with respect to FIGS. 6C and 6D. The peak RF frequencies in both scan directions are minimized and equalized after application of third harmonic (300 kHz). As shown, the forward scan duration 75 and the backward scan duration 77 are substantially identical. The frequency marker at peak RF of backward scan 80 has a frequency of about 285.31 MHz. Similarly, the frequency marker at peak RF of forward scan 83 has a frequency of about 280.27 MHz. The ratio of 280.27 MHZ to 285.31 MHz is about 0.98. The closeness of these values and the minimization of these values for the drive waveform of FIG. 7 shows a significant improvement relative to the frequency marker at peak RF of the backward scan having a frequency of about 462.9 MHz in FIG. 2 while the frequency marker at peak RF of the forward scan had a frequency of about 246.88 MHz to yield a comparative ratio of about 1.875 (backward/forward) or about 0.53 (forward/backward).

Figure 8A:
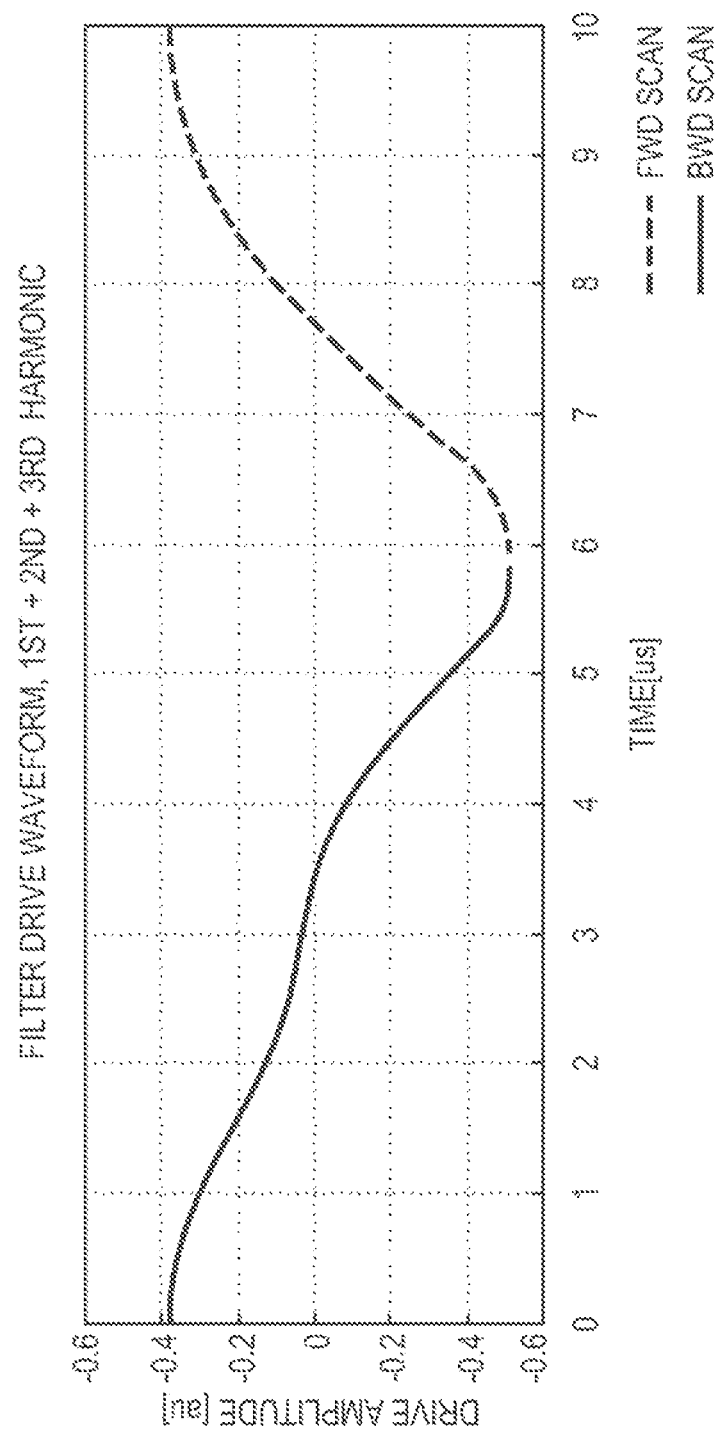
FIG. 8A shows a plot of drive amplitude versus time with respect to a drive waveform composed of three harmonics according to an illustrative embodiment of the invention.

FIG. 8A shows a drive waveform generated using three sine waves using one or more of the steps of FIG. 1B. The AC component has been normalized. In addition, the AC gain and DC bias were readjusted to obtain a 100 nm tuning range centered near 1310 nm.

Figure 8B:
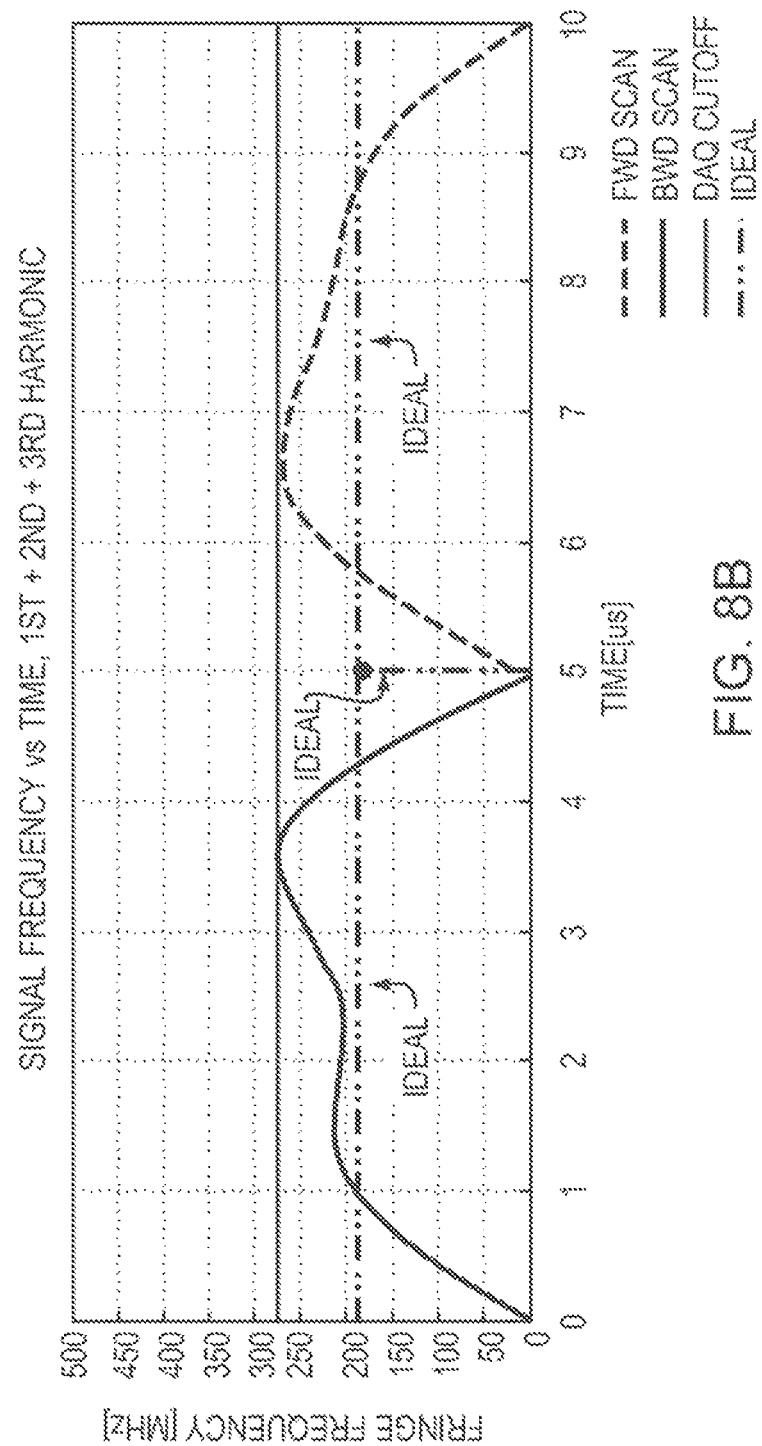
FIG. 8B shows a plot of measured signal frequency versus time with respect to a drive waveform according to an illustrative embodiment of the invention.

FIG. 8B shows the measured instantaneous frequency using the drive waveform of FIGS. 7 and 8A applied to a VCSEL. The forward and backward scans are symmetric and have minimum peak RF frequency. The duration of the forward scan of about 5.00 microseconds is the same as the backward scan duration of about 5.00 microseconds, thus the comparative ratio is 1. In turn, the peak radiofrequency of the forward scan of about 268 MHz is about the same as the peak radiofrequency of the backward scan of about 275 MHz. In addition, the both the forward scan and the backward scan are at or below the DAQ cutoff resulting in a useable line rate of 200 kHz and an effective duty cycle of about 100%.

Figure 9A:
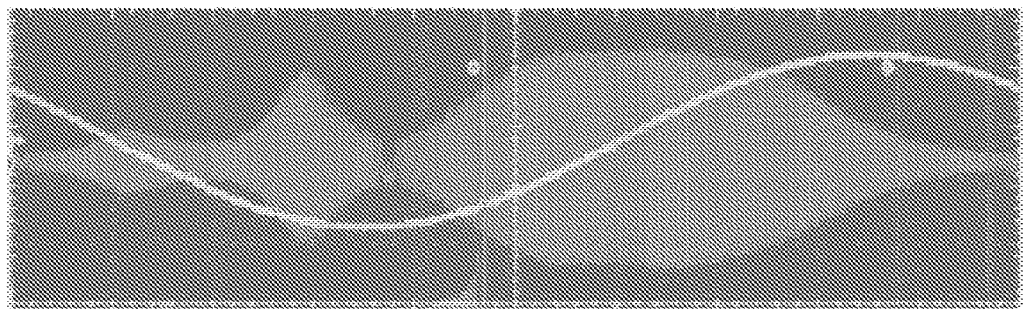
FIGS. 9A-9C show three respective drive waveforms of increasing suitability for use with an optical coherence tomography system in accordance with an illustrative embodiment of the invention.
Figure 9B:
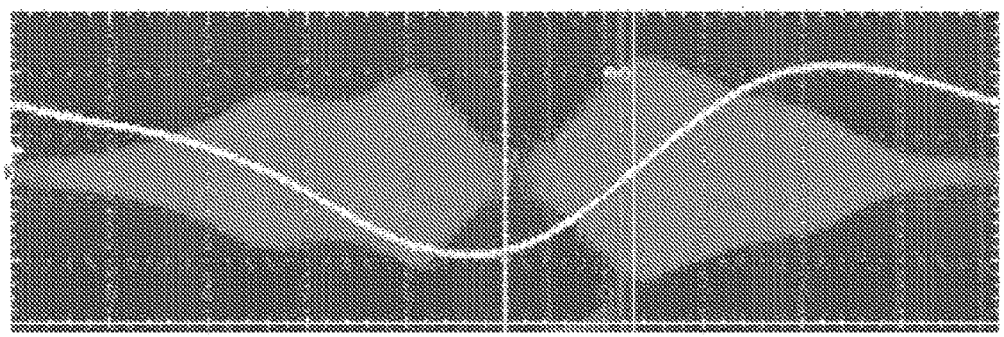
Figure 9C:
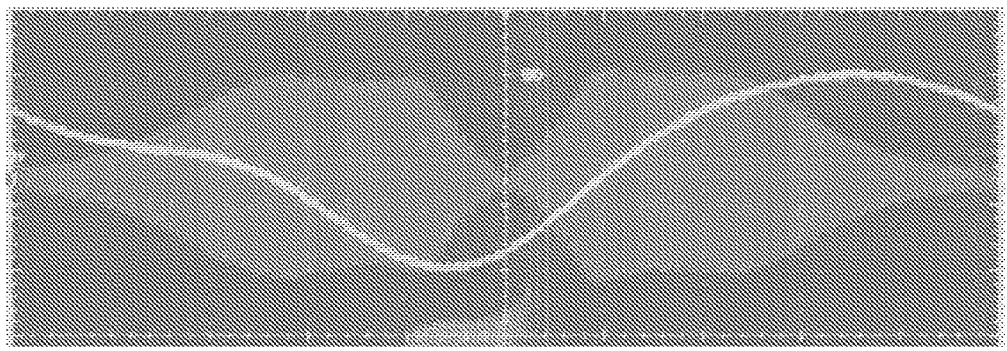

FIGS. 9A-9C show three plots of the drive waveforms of FIGS. 2, 5, and 7, respectively. The amplitude along the vertical axis is in units of about 300 millivolts per unit division and time is shown along the horizontal axis in units of 1 microsecond per unit division The changes in the drive waveform over time occur as a result of the addition of the different optimized harmonics as discussed herein.

In one embodiment, the DC bias of the fundamental wave ranges from about 0 to about 200 V. In one embodiment, the amplitude of the fundamental wave ranges from about 0 to about 200 V. In one embodiment, the tuning range ranges from about 20 to about 200 nm. In one embodiment, the phase of the fundamental wave ranges from about 0 to about $2\pi$ radians. In one embodiment, the phase of the second harmonic ranges from about 0 to about $2\pi$ radians. In one embodiment, the phase of the third harmonic ranges from about 0 to about $2\pi$ radians. In one embodiment, the amplitude of the second harmonic ranges from about 0 to about 200 V. In one embodiment, the amplitude of the third harmonic ranges from about 0 to about 200 V.

In one embodiment, the drive waveform described herein is configured to have a 100% duty cycle at 100 kHz drive frequency. In one embodiment, the drive waveform described herein is configured to have substantially symmetric or symmetric forward and backward sweeps. In one embodiment, the drive waveform described herein is configured to have a 200 kHz effective sweep rate. In one embodiment, the drive waveform described herein is configured to have a RF signal frequency ≤ about 275 MHz at about 8 mm imaging range and about a 100 nm tuning range.

In the description, the invention is discussed in the context of optical coherence tomography; however, these embodiments are not intended to be limiting and those skilled in the art will appreciate that the invention can also be used for other imaging and diagnostic modalities or optical systems in general.

The terms light and electromagnetic radiation are used interchangeably herein such that each term includes all wavelength (and frequency) ranges and individual wavelengths (and frequencies) in the electromagnetic spectrum. Similarly, the terms device and apparatus are also used interchangeably. In part, embodiments of the invention relate to or include, without limitation: sources of electromagnetic radiation and components thereof; systems, subsystems, and apparatuses that include such sources; mechanical, optical, electrical and other suitable devices that can be used as part of or in communication with the foregoing; and methods relating to each of the forgoing. Accordingly, a source of electromagnetic radiation can include any apparatus, matter, system, or combination of devices that emits, re-emits, transmits, radiates or otherwise generates light of one or more wavelengths or frequencies.

One example of a source of electromagnetic radiation is a laser. A laser is a device or system that produces or amplifies light, by the process of stimulated emission of radiation. Although the types and variations in laser design are too extensive to recite and continue to evolve, some non-limiting examples of lasers suitable for use in embodiments of the invention can include tunable lasers (sometimes referred to as swept source lasers), superluminescent diodes, laser diodes, semiconductor lasers, mode-locked lasers, gas lasers, fiber lasers, solid-state lasers, waveguide lasers, laser amplifiers (sometimes referred to as optical amplifiers), laser oscillators, and amplified spontaneous emission lasers (sometimes referred to as mirrorless lasers or superradiant lasers).

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Non-Limiting Software Embodiments for Implementing Drive Wavefront Generation

The present invention may be embodied in many different forms, including, but in no way limited to, computer program logic for use with a processor (e.g., a microprocessor, microcontroller, digital signal processor, or general purpose computer), programmable logic for use with a programmable logic device, (e.g. a Field Programmable Gate Array (FPGA) or other PLD), discrete components, integrated circuitry (e.g., an Application Specific Integrated Circuit (ASIC)), or any other means including any combination thereof. In one embodiment of the present invention, some or all of the processing of the data used to generate or design a drive waveform or component thereof is implemented as a set of computer program instructions that is convened into a computer executable form, stored as such in a computer readable medium, and executed by a microprocessor under the control of an operating system. Control and operation of components of a given light source, such as a laser, such as a VCSEL, can also be so controlled or operated using a computer. In one embodiment, light source, drive waveform, control system data, or tunable filter parameters are transformed into processor understandable instructions suitable for generating drive signals for tunable filters, operating a light source for an OCT system with a suitable duty cycle, controlling a tunable filter, signal processing, function generation, sweeping a tunable filter in a first direction or in a first direction and a second direction and other features and embodiments as described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink-wrapped software), preloaded with a computer system (e.g. on system ROM or fixed disk), or distributed over a network.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, function generator data, harmonic wave data, tunable filter data, frequencies, interferometer signal data, filter drive signals, linear drive signals, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiment, are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

What is claimed is:

1. An optical coherence tomography system comprising
   a drive waveform source comprising a memory, an output, and one or more function generators configured to (a) generate a first harmonic wave, (b) generate a second harmonic wave (c) generate a third harmonic wave; and
   (d) combine the first, second, and third harmonic waves such that a drive waveform is generated and stored in the memory, the drive waveform configured to cause a sweep response in a forward scan direction of the light source and a sweep response in a backward scan direction of the light source to be substantially symmetric and substantially linearize a sweep response of the light source; and a light source comprising a tunable filter having an asymmetric sweep response, the tunable filter in electrical communication with the output and configured to receive the drive waveform from the output, wherein the second harmonic wave has a first phase value configured to cause a peak RF frequency for a backward scan of the tunable filter and a peak RF frequency for a forward scan of the tunable filter to differ by less than about 15%.

2. The system of claim 1 wherein the drive waveform source is a control system, a processor or a circuit.

3. The system of claim 1 wherein the light source is a laser.

4. The system of claim 3 wherein the tunable filter is a MEMS tunable filter.

5. The system of claim 3 the tunable filter is a piezoelectric tunable filter.

6. The system of claim 3 wherein the third harmonic wave has a second phase value configured to reduce or minimize a peak RF OCT signal frequency for a backward scan and a forward scan of the tunable filter.

7. The system of claim 3 wherein the third harmonic wave has a first amplitude value configured to reduce or minimize a peak RF OCT signal frequency for a backward scan and a forward scan of the tunable filter.

8. The system of claim 1 wherein the first phase value is generated by searching for an extremum in a two dimensional space that includes forward and backward scan data measured with respect to the light source as the tunable filter is swept.

9. The system of claim 1 wherein the first amplitude value is generated by searching for an extremum in a two dimensional space that includes forward and backward scan data measured with respect to the light source as the tunable filter is swept.

10. The system of claim 3 wherein an effective duty cycle of the laser is greater than about 90% of a sweep period of the light source when collecting OCT data.

11. The system of claim 3 wherein a forward scan duration of the tunable filter is about equal to a backward scan duration of the tunable filter.

12. The system of claim 1 wherein a ratio of a forward scan duration to a backward scan duration ranges from about 0.8 to about 1.2 when the drive waveform is applied to the tunable filter.

13. The system of claim 1 wherein a ratio of a peak RF fringe frequency during a forward scan to a peak RF fringe frequency during a backward scan duration ranges from about 0.9 to about 1.1 when the drive waveform is applied to the tunable filter.

14. The system of claim 1 wherein a sweep response in a forward scan direction of the light source and a sweep response in a backward scan direction of the light source is substantially symmetric when the tunable filter receives the drive waveform.

15. The system of claim 9 wherein the two dimensional space is an amplitude and phase space.

16. An optical coherence tomography system comprising:

a swept light source comprising a tunable filter comprising an input, the tunable filter in optical communication with a sample arm of an interferometer, wherein the tunable filter is drivable bidirectionally and has an asymmetric sweep response;

a control system comprising a non-transitory memory and an output, wherein the output is in electrical communication with the input, the control system configured to drive the tunable filter in one or more directions; and a drive waveform stored in the non-transitory memory, the drive waveform configured to cause a sweep response in a forward scan direction of the light source and a sweep response in a backward scan direction of the swept light source to be substantially symmetric and substantially linearize a sweep response of the light source, wherein an effective duty cycle of the swept light source is greater than about 90% of a sweep period of the swept light source when collecting optical coherence tomography data.

17. The system of claim 16 wherein a ratio of a forward scan duration to a backward scan duration ranges from about 0.8 to about 1.2 when the drive waveform is applied to the tunable filter.

18. The system of claim 16 wherein a ratio of a peak RF fringe frequency during a forward scan to a peak RF fringe frequency during a backward scan duration ranges from about 0.9 to about 1.1 when the drive waveform is applied to the tunable filter.

19. The system of claim 16 wherein a forward scan duration of the tunable filter is about equal to a backward scan duration of the tunable filter.

20. The system of claim 16 wherein a sweep response in a forward scan direction of the swept light source and a sweep response in a backward scan direction of the swept light source is substantially symmetric when the tunable filter receives the drive waveform.

21. The system of claim 16 wherein the stored drive waveform is generated by superimposing two or more harmonic waves, the two or more harmonic waves defined using a phase value and an amplitude value.

22. The system of claim 21 wherein the phase value is selected to reduce or minimize a peak RF OCT signal frequency for a backward scan and a forward scan of the tunable filter.

23. The system of claim 21 wherein the amplitude value is selected to reduce or minimize a peak RF OCT signal frequency for a backward scan and a forward scan of the tunable filter.

* * * * *